US010500153B2

(12) United States Patent
García Sanz et al.

(10) Patent No.: US 10,500,153 B2
(45) Date of Patent: Dec. 10, 2019

(54) EXOPOLYSACCHARIDE FOR THE TREATMENT AND/OR CARE OF THE SKIN, CULTURE MEDIA AND COMPOSITIONS

(71) Applicant: Lipotec, S.A.U., Gavà (ES)

(72) Inventors: Núria García Sanz, Gavà (ES); Antonio Vicente Ferrer Montiel, Alicante (ES); Albert Soley Astals, Gavà (ES); Nuria Almiñana Doménech, Gavà (ES)

(73) Assignee: Lipotec SAU, Barcelona (ES)

( * ) Notice: Subject to any disclaimer, the term of this patent is extended or adjusted under 35 U.S.C. 154(b) by 0 days.

(21) Appl. No.: 15/032,840

(22) PCT Filed: Oct. 30, 2014

(86) PCT No.: PCT/EP2014/073401
§ 371 (c)(1),
(2) Date: Apr. 28, 2016

(87) PCT Pub. No.: WO2015/063240
PCT Pub. Date: May 7, 2015

(65) Prior Publication Data
US 2016/0263014 A1 Sep. 15, 2016

(30) Foreign Application Priority Data
Oct. 30, 2013 (EP) .................................. 13382437

(51) Int. Cl.
A61K 8/99 (2017.01)
C12P 19/04 (2006.01)
A61Q 19/06 (2006.01)
A61Q 19/08 (2006.01)
A61K 8/14 (2006.01)
A61K 8/34 (2006.01)
A61K 8/55 (2006.01)
A61K 8/73 (2006.01)
A61K 8/86 (2006.01)
A61K 8/891 (2006.01)
A61K 8/02 (2006.01)
A61K 8/04 (2006.01)
A61K 8/06 (2006.01)
A61K 8/37 (2006.01)

(52) U.S. Cl.
CPC ............. A61K 8/99 (2013.01); A61K 8/0216 (2013.01); A61K 8/042 (2013.01); A61K 8/068 (2013.01); A61K 8/14 (2013.01); A61K 8/34 (2013.01); A61K 8/342 (2013.01); A61K 8/375 (2013.01); A61K 8/55 (2013.01); A61K 8/73 (2013.01); A61K 8/86 (2013.01); A61K 8/891 (2013.01); A61Q 19/06 (2013.01); A61Q 19/08 (2013.01); C12P 19/04 (2013.01); A61K 2800/5426 (2013.01); A61K 2800/596 (2013.01); A61K 2800/75 (2013.01); A61K 2800/78 (2013.01); A61K 2800/85 (2013.01)

(58) Field of Classification Search
None
See application file for complete search history.

(56) References Cited

FOREIGN PATENT DOCUMENTS

WO    WO 2012/072245    *  6/2012

OTHER PUBLICATIONS

Mata et al. Exopolysaccharide produced by the recently described halophilic bacteria Halomonas ventosae and Halomonas anticariensis, Research in Microbiology, 157, (2006).*
Dupressoir, et al., "Characterization of a mammalian gene related to the yeast CCR4 general transcription factor and revealed by transposon insertion", J. Biol. Chem. vol. 274(43), pp. 31068-31075(1999).
Dupressoir, et al., "Identification of four families of yCCR4- and $Mg^{2+}$-dependent endonuclease-related proteins in higher eukaryotes, and characterization of orthologs of yCCR4 with a conserved leucine-rich repeat essential for hCAF1/hPOP2 binding", BMC Genomics, vol. 2:9, pp. 1-14(2001).
Green, et al., "Loss of Nocturnin, a circadian deadenylase, confers resistance to hepatic steatosis and diet-induced obesity", Proc. Nat. Acad. Sci. USA, vol. 104(23), pp. 9888-9893(2007).
Boivin, et al., "Circadian clock genes oscillate in human peripheral blood mononuclear cells", Blood Dec. 2003, vol. 102(12), pp. 4143-4145 (2003).
Green, et al., "The Meter of Metabolism," Cell, vol. 134(5), pp. 728-742 (2008).
Kawai, et al., "PPARγ: a circadian transcription factor in adipogenesis and osteogenesis", Nat. Rev. Endocrinol., vol. 6, pp. 629-636 (2010).
Green, et al., "Identification of a novel vertebrate circadian clock-regulated gene encoding the protein Nocturnin", Proc. Nat. Acad. Sci. USA, vol. 93(25), pp. 14884-14888 (1996).
Niu, et al., "The circadian deadenylase Nocturnin is necessary for stabilization of the iNOS mRNA in mice" PloS one 2011, vol. 6(11), pp. 1-9 (2011).
Wilkinson, et al., "Harry's Cosmeticology", Seventh edition, ed. Longman House, Essex, GB, pp. 50-72, and 757-799(1982).
Schaab, Impregnating Fabrics with Microcapsules, HAPPI, pp. 84-86 (1986).
Nelson, et al., "Application of microencapsulation in textiles", Int. J. Pharm., vol. 242(1-2), pp. 55-62 (2002).
Hipler, et al., "Biofunctional Textiles and the Skin" Curr. Probl. Dermatol. vol. 33, Basel, Switzerland, pp. 35-41(2006).
Malcolm, et al., Controlled release of a model antibacterial drug from a novel self-lubricating silicone biomaterial, J. Cont. Release, vol. 97(2), pp. 313-320 (2004).

(Continued)

Primary Examiner — David J Blanchard
Assistant Examiner — Sarah J Chickos
(74) Attorney, Agent, or Firm — Thoburn Dunlap; Ann Skerry

(57) ABSTRACT

Exopolysaccharide of a bacterial strain for its use in treatment and/or care of the skin, as well as its cosmetic and/or dermopharmaceutical compositions. In particular, its use for inflammation, lipolysis, lipid accumulation and skin firmness.

26 Claims, No Drawings

(56) References Cited

OTHER PUBLICATIONS

Gottschlack, et al., "CTFA International Cosmetic Ingredient Dictionary & Handbook," 12th Edition, vol. 3, pp. 3040-3065 (2008).
Kamerling, et al., "Characterization by Gas-Liquid Chromatography—Mass Spectrometry and Proton-Magnetic-Resonance Spectroscopy of Pertrimethylsilyl Methyl Glycosides obtained in the Methanolysis of Glycoproteins and Glycopeptides," Biochem. J., vol. 151, pp. 491-495 (1975).
Montreuil, et al., "Glycoproteins," Carbohydrate analysis: a practical approach, Eds Chaplin and Kennedy, I.R.L Press, Oxford, Washington D.C., Chapter 5, pp. 143-204 (1986).
Escudero et al., "Optimization of carbohydrate silylation for gas chromatography," J. Chromatogr. A., vol. 1027, pp. 117-120 (2004).
Béjar, et al., "Characterization of exopolysaccharides produced by 19 halophilic strains of the species *Halomonas eurihalina*," Journal of Biotechnology, vol. 61, pp. 135-141 (1998).
Iyer, et al., "Emulsifying properties of a marine bacterial exopolysaccharide," Enzyme and Microbial Technology, vol. 38, pp. 220-222 (2006).
Martínez-Canovas, et al., "A Taxonomic Study to Establish the Relationship between Exopolysaccharide-Producing Bacterial Strains Living in Diverse Hypersaline Habitats," Current Microbiology, vol. 48, pp. 348-353 (2004).

\* cited by examiner

EXOPOLYSACCHARIDE FOR THE TREATMENT AND/OR CARE OF THE SKIN, CULTURE MEDIA AND COMPOSITIONS

This application claims the benefit of PCT/EP2014/073401, filed Oct. 30, 2014, and EP13382437.5, filed Oct. 30, 2013, from which the PCT application claims priority, the disclosures of which are incorporated herein by reference in their entireties.

FIELD OF THE INVENTION

The disclosed technology relates to an exopolysaccharide of bacterial origin, which reduces lipid accumulation. Said product is secreted by a strain of the *Halomonas anticariensis* species. This invention also relates to the use of said exopolysaccharide of bacterial origin in cosmetic or dermopharmaceutical compositions for the treatment and/or care of the skin, mucous membranes and/or hair.

BACKGROUND OF THE INVENTION

The skin, mucous membrane, hair and/or the nails constitute a physical barrier between an organism and their environment. The skin is composed of two tissues: the epidermis and the dermis. The dermis forms approximately 90% of the thickness of the skin, containing collagen, elastin, several differentiated structures such as blood vessels, sweat glands, and mainly cell-types such as fibroblasts, macrophages and adipocytes.

In the skin, the adipocytes are located in the deepest layers of the dermis, the hypodermis. The adipocytes are organized in lobules, separated by septa of connective tissue that contain vessels, nerves and lymph nodes. The main function of the adipocytes is the storage of fat in vacuoles in the form of triglycerides. In addition to this energy-related function, these cells are also involved in the production of some hormones (estrogen) as well as in the synthesis of molecules implicated in inflammatory response.

One of the disorders related to the adipose cells of the hypodermis that has been highly focused on by the cosmetic industry, is cellulite. Cellulite is the result of an excessive accumulation of lipids in the adipose tissue which puts a considerable amount of pressure on the surrounding epithelial tissue, resulting in an irregular appearance of the skin with the presence of dimples. From an aesthetic point of view this appearance has been named orange peel.

For the treatment of this problem, a number of agents exists that stimulate lipolysis by reducing the volume of accumulated lipids, thus showing a draining effect which reduces the volume by eliminating retained water stored between the tissues. Furthermore, other agents with firming effect in the treatment of cellulite can also be used that correct the irregular appearance of the skin.

The most widely used anti-cellulite agent is caffeine due to its lipolytic effects in adipocytes [Vogelgesang B. et al., "*In vitro and in vivo efficacy of sulfo-carrabiose a sugar-based cosmetic INGREDIENTS with anti-cellulite properties*", Int. J. Cosmet. Sci., 2011, 33(2), 120-5; Nakabayashi H. et al., "*Inhibitory effects of caffeine and its metabolites on intracellular lipid accumulation in murine 3T3-L1 adipocytes*", Biofactors, 2008, 34(4), 293-302], in addition to its draining effects. Furthermore, a high number of alternative agents also exist that possess similar mechanisms. A recent strategy in the search for new anti-cellulite agents is based on the influence over the actions related to circadian rhythms in the skin, [Dupressoir A. et al., "*Characterization of a mammalian gene related to the yeast CCR4 general transcription factor and revealed by transposon insertion*", J. Biol. Chem. 1999, 274(43), 31068-75; Dupressoir A. et al., "*Identification of four families of yCCR4- and Mg²⁺-dependent endonuclease-related proteins in higher eukaryotes, and characterization of orthologs of yCCR4 with a conserved leucine-rich repeat essential for hCAF1/hPOP2 binding*", BMC Genomics, 2001, 2:9; Green C. B. et al., "*Loss of Nocturnin, a circadian deadenylase, confers resistance to hepatic steatosis and diet-induced obesity*", Proc. Nat. Acad. Sci. USA, 2007, 104(23), 9888-93] which similar to other tissues, experiences functional variations due to changes between day and night.

In humans, as well as other animal species, a large portion of their social behavior and their physiological functions vary from day to night in a rhythmic fashion. The system that defines the circadian clock comprises central and peripheral components. In mammals, the central component of this oscillatory system resides in the suprachiasmatic nucleus (SCN) of the anterior hypothalamus [Boivin D. B. et al., "*Circadian clock genes oscillate in human peripheral blood mononuclear cells*", Blood 2003, December, 102(12), 4143-4145]. This nucleus mainly functions by reception of light signals from specialized retina cells, the retina ganglion cells and activating a series of transcriptional, translational, and posttranslational mechanisms involving several genes, such as CLOCK, BMAL1, PER, and CRY that result in cascades of gene expression with 24 hr periodicity. Green C. B. et al., "*The Meter of Metabolism*", Cell, 2008, 134(5), 728-742]. Peripheral tissues and organs also possess autonomous regulatory systems that are independent of the central clock, but use the same machinery of genes and show entrainment to external stimuli that the tissue may be subject to [Kaway M. and Rosen C. J., "*PPARγ: a circadian transcription factor in adipogenesis and osteogenesis*", Nat. Rev. Endocrinol., 2010, 6, 629-636].

Some functions that intervene in the regulation of circadian rhythms, or which are subject to them, are the production of hormones, cytokine levels, temperature regulation or glucose levels, amongst others [Mehling A. and Fluhr J. W., "*Chronobiology: biological clocks and rhythms of the skin*", Skin Pharmacol. Physiol, 2006, 19(4), 182-9].

Several of the skin's functions are also subject to circadian rhythms, similar to that occurring in other organs. Thus, it has been observed that various parameters investigated in woman, such as blood circulation, amino acid content and Transepidermal Water Loss (TEWL) increase during the night. On the other hand, the production of sebum, measured on the forehead using a sebumeter, gives its highest values around midday. The pH of the skin tends to decrease throughout the night then increase throughout the day. The skin's blood circulation demonstrates circadian rhythms and ranges during the day from low circulation early morning to then increasing, reaching its maximum values in the final hours of the afternoon going on to evening. Interestingly, the circadian rhythms can also be found at cellular level in the skin, as it has been observed that proliferation of epidermal cells demonstrates its highest values at around 11 pm. [Mehling A. and Fluhr J. W., "*Chronobiology: biological clocks and rhythms of the skin*", Skin Pharmacol. Physiol, 2006, 19(4), 182-9].

One of the nocturnal functions in which an effect has been observed is that of adipogenesis, as one of the genes studied with such effect is nocturnin. Thus, in some of the first studies carried out with *Xenopus laevis* retina that aimed to isolate genes affected by circadian rhythms, it was observed that the expression nocturnin mRNA was present at high levels in early night. [Green C. B. and Besharse J. C., "*Identification of a novel vertebrate circadian clock-regulated gene encoding the protein Nocturnin*", Proc. Nat. Acad. Sci. USA, 1996, 93(25), 14884-8]. On the other hand, it was later found that in addition to being expressed in the retina in rats, nocturnin mRNA was expressed in numerous tissues, such as the liver, brain, lung, heart, ovary, skeletal muscle, testicles and bone marrow. Similarly, it was observed that a great circadian variation existed in the expression of nocturnin mRNA, with its maximum levels occurring at the beginning of the night [Dupressoir A. et al., "*Characterization of a mammalian gene related to the yeast CCR4 general transcription factor and revealed by transposon insertion*", J. Biol. Chem. 1999, 274(43), 31068-75; Dupressoir A. et al., "*Identification of four families of yCCR4- and $Mg^{2+}$-dependent endonuclease-related proteins in higher eukaryotes, and characterization of orthologs of yCCR4 with a conserved leucine-rich repeat essential for hCAF1/hPOP2 binding*", BMC Genomics, 2001, 2:9].

Regarding the function of nocturnin, studies with knock out mice that are unable to express nocturnin demonstrated that, even though these individuals showed normal general circadian behavior, they presented resistance to diet-induced obesity and they also showed other metabolic changes such as a lower accumulation of lipids in the liver. Therefore, this metabolic phenotype suggests that nocturnin controls specific secondary circadian channels associated with the accumulation and use of lipids. [Green C. B. et al., "*Loss of Nocturnin, a circadian deadenylase, confers resistance to hepatic steatosis and diet-induced obesity*", Proc. Nat. Acad. Sci. USA, 2007, 104(23), 9888-93]. Another one of the functions in which nocturnin's involvement has been observed is inflammation. Nocturnin stabilizes the pro-inflammatory transcript iNOS and a reduction in nocturnin would mean a reduction in inflammation. [Niu S. et al., "*The circadian deadenylase Nocturnin is necessary for stabilization of the iNOS mRNA in mice*" PloS one 2011, 6(11), e26954].

As nocturnin is a marker that is correlated with the accumulation and use of lipids, it may be used as a base for further studies to identify stimulation or reduction activity on the accumulation of lipids in adipocytes in the dermis and in the treatment of inflammation.

Surprisingly, the applicant of this invention has found an exopolysaccharide of bacterial origin that is an alternative to the problems in the state of the art previously mentioned regarding the accumulation of lipids, cellulite, inflammation or lipolysis, amongst others.

SUMMARY OF THE INVENTION

The disclosed technology provides a solution for the problem of lipid accumulation and cellulite by the use of the exopolysaccharide excreted by a strain of *Halomonas anticariensis* species.

DESCRIPTION OF THE INVENTION

This invention relates to the exopolysaccharide excreted by a strain of *Halomonas anticariensis* species, to the exopolysaccharide for its use in the therapeutic treatment of the skin, to the use of the exopolysaccharide for the cosmetic, non-therapeutic treatment and/or care of the skin and pharmaceutical, cosmetic or dermopharmaceutical compositions which comprise the exopolysaccharide. Surprisingly the inventors of this invention have found that the aforementioned exopolysaccharide reduces the lipid accumulation. In particular, the decrease in the level of nocturnin protein reduces the lipid accumulation in the skin.

Definitions

In order to facilitate the comprehension of this invention, the meanings of some terms and expressions as used in the context of the invention are included.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

In the context of this invention the terms "produced" and "excreted" are used indistinctly.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term "skin" includes the scalp.

The term "treatment", as used in the context of this specification when it is not accompanied by the qualifications "cosmetic, non-therapeutic", means the administration of a compound according to the invention to alleviate or eliminate a disease or disorder or reduce or eliminate one or more symptoms associated with this disease or disorder. The term "treatment" also covers the ability to alleviate or eliminate the physiological consequences of the disease or disorder.

When the term "treatment" is accompanied by the qualifications "cosmetic, non-therapeutic" they refer to the application of the compound to the skin in particular with the aim of improving the cosmetic qualities of the skin such as and not restricted to, their level of hydration, elasticity, firmness, shine, tone or texture, among others. The term "care" in this invention refers to the maintenance of the qualities of the skin and it includes the body and/or hair hygiene. These qualities are subject to improvement and maintained through a cosmetic treatment and/or care of the skin both in healthy subjects as well as those which present diseases and/or disorders of the skin, such as and not restricted to, ulcers and lesions on the skin, psoriasis, dermatitis, acne or rosacea, among others.

The term "prevention", as used in this invention, refers to the ability of a compound of the invention to prevent, delay or hinder the appearance or development of a disease or disorder before its appearance.

In the context of this invention, the term "aging" refers to the changes experienced by the skin with age (chronoaging) or through exposure to the sun (photoaging) or to environmental agents such as tobacco smoke, extreme climatic conditions of cold, heat, or wind, chemical contaminants or pollutants, and includes all the external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, the appearance of bags under the eyes or the appearance of a double chin, among others, changes to the color of the skin such as spots, reddening, bags under the eyes or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, hypodermis, dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and presents the same physical characteristics as aging, such as and not restricted to, flaccidity, sagging, changes to the color or irregularities in the pigmentation, abnormal and/or excessive keratinization.

Therefore, a first aspect of the present invention relates to the exopolysaccharide excreted by a strain of *Halomonas anticariensis* species for its use in the treatment of the skin. In particular, the treatment refers to the treatment of inflammation in the skin, and/or re-epithelialization and/or wound healing of the skin. In particular the inflammation is selected, for example and not restricted to, from the group formed by psoriasis, sensitive skin, dermatitis, atopic dermatitis, contact dermatitis, diaper dermatitis, seborrheic dermatitis, eczema, rosacea, acne, hyperproliferative skin disease, burns, sunburn, paronychia, skin inflammation after surgery, after treatment with intense pulsed light therapy (IPL), after treatment with monochromatic pulsed light therapy (laser), after treatment with chemical peeling agents or after overexposure to aggressive external agents, among others.

In another aspect, the present invention relates to the use of the exopolysaccharide excreted by a strain of *Halomonas anticariensis* species for the cosmetic, non-therapeutic treatment and/or care of the skin, in particular for the treatment and/or prevention of cellulite, treatment of reduction of lipid accumulation in the skin, stimulation of lipolysis in the skin, stimulation of collagen synthesis, treatment and/or prevention of skin aging, treatment and/or prevention of skin wrinkles, treatment for improving skin firmness, for the prevention of loss of skin firmness and/or treatment for improving skin elasticity.

Preferably, the treatment, the cosmetic, non-therapeutic treatment and/or care of the skin reduces the amount of nocturnin in the cells.

In another particular embodiment, the treatment and/or care of the skin is carried out by topical or transdermal application.

In another particular embodiment, the strain of *Halomonas anticariensis* species is a strain of *Halomonas anticariensis* species with deposit number LMG P-27891. Said strain has been deposited on Sep. 18, 2013 at the Belgian Coordinated Collection of Microorganisms (BCCM)/Laboratorium voor Microbiologie-Bacteriëverzameling (LMG) (BCCM/LMG) (University Ghent, K. L. Ledeganckstraat 35, B-9000 Ghent, Belgium) as institution legally recognized for said purpose according to the Budapest Treaty on the International Recognition of the Deposit of Microorganisms on Apr. 28, 1977.

In a preferred embodiment, the exopolysaccharide excreted by the bacterial strain of *Halomonas anticariensis* species contains the monosaccharides glucose, mannose and rhamnose. In particular, the strain of *Halomonas anticariensis* species is a strain of *Halomonas anticariensis* species with deposit number LMG P-27891. More preferably, the exopolysaccharide of this invention shows a composition in weight of 1% to 22% of glucose, 50% to 85% of mannose, 15% to 30% of rhamnose, with the condition that the sum of the percentages does not exceed 100%. Even more preferably, the exopolysaccharide shows a composition in weight of 1.5% to 20% of glucose, 55% to 80% of mannose, 18% to 26% of rhamnose. Even more preferably, the exopolysaccharide shows a composition in weight of 1.5% to 18% of glucose, 58% to 78% of mannose, 20% to 25% of rhamnose. Optionally the exopolysaccharide in addition contains up to 3% of galacturonic acid and/or up to 4% of xylose, preferably less than 2% of galacturonic acid and less than 2% of xylose, and more preferably less than 1% of galacturonic acid and less than 1% of xylose.

In another particular embodiment, the exopolysaccharide excreted by the bacterial strain of *Halomonas anticariensis* species has a residence time between 4 and 10 minutes, and more preferably between 5 and 9 minutes at a chromatographic analysis High Performance Liquid Chromatography (HPLC), with a chromatographic column PL AQUAGEL-OH™ 8 µm AQUEOUS SEC COLUMNS and water with sodium acetate 0.1 M as eluent and flow rate 0.8 ml/min. PL AQUAGEL-OH™ 8 um AQUEOUS SEC COLUMNS is a column for aqueous Size Exclusion Chromatography, with a packaging having the capacity to separate compounds depending on its MW, applied to neutral, anionic and cationic water-soluble polymers and with a particle size of 8 µm, a pore size of 50 Å and a length/Internal Diameter of 300 mm×7.5 mm.

In another particular embodiment, the exopolysaccharide can be obtained through fermentation of the strain of *Halomonas anticariensis* species in a suitable culture medium, conventionally stirred and aerated for synthesizing and secreting said product to the culture medium followed by the isolation and purification. Fermentation to produce the exopolysaccharide of this invention can be carried out in a medium stirred and aerated at a temperature between 15° C. and 40° C., preferably at 32° C., the medium having a pH between 5.5 and 9, preferably around 7.0, adjusting it if necessary during fermentation. The duration of the fermentation is between 12 to 120 hours, preferably between 24 and 72 hours.

In another particular embodiment, in the fermentation of the strain of *Halomonas anticariensis* species a culture medium containing exogenous sugars, such as and not restricted to, galactose, glucose, mannose, amygdalin, cellobiose, maltose, starch, glycogen, lactose, mixtures thereof and/or extracts containing mixtures of these sugars can be used as a carbon source. In particular, an exogenous supply of glucose of 2 to 40 g/L, and preferably from 5 to 25 g/L is provided.

In another particular embodiment, the culture medium may comprise additional nitrogen or carbon sources such as yeasts extracts, malt extracts or peptones, with concentrations of each one of these components of 0.1 to 20 g/L, and preferably from 0.5 to 10 g/L.

In another particular embodiment, mineral salts are also provided for the fermentation culture of the strain of *Halomonas anticariensis* species and they are selected from among salts which provide the ions $Na^+$, $K^+$, $NH_4^+$, $Ca^{2+}$, $Mg^{2+}$, $PO_4^{3-}$, $SO_4^{2-}$, $Cl^-$, $CO_3^{2-}$, or trace elements such as Cu, Mn, Fe and Zn.

In another particular embodiment, the method of isolation and purification of the exopolysaccharide is carried out by the methods known by the person skilled in the art such as, centrifugation, filtration, ultrafiltration and dialysis. Preferably ultrafiltration and dialysis are carried out with a polyethersulfone membrane which retains molecules of a molecular weight greater than 10,000 Da. Preferably, centrifugation and filtration steps are directed to separate the strain of the *Halomonas anticariensis* species from the supernatant where the exopolysaccharide is found. In other preferred embodiment, the exopolysaccharide is purified by precipitation via addition of ethanol, acetone or isopropanol. In particular, the strain of *Halomonas anticariensis* species is a strain of *Halomonas anticariensis* species with deposit number LMG P-27891.

In another particular embodiment, the exopolysaccharide produced by a strain of *Halomonas anticariensis* species is contained in a cosmetic or dermopharmaceutical composition characterized in that it comprises a cosmetically or dermopharmaceutically effective quantity of the exopolysaccharide and at least one cosmetically and/or dermopharmaceutically acceptable excipient and/or ingredient. In particular, the strain of *Halomonas anticariensis* species is a strain of *Halomonas anticariensis* species with deposit number LMG P-27891.

Another aspect of this invention relates to a cosmetic or dermopharmaceutical composition characterized in that it comprises a cosmetically or dermopharmaceutically effective quantity of the exopolysaccharide produced by a strain of *Halomonas anticariensis* species and at least one cosmetically and/or dermopharmaceutically acceptable excipient and/or ingredient. In particular, the strain of *Halomonas anticariensis* species is a strain of *Halomonas anticariensis* species with deposit number LMG P-27891. Said compositions can be prepared by the conventional methods known by the persons skilled in the art ["*Harry's Cosmeticology*", Seventh edition, (1982), Wilkinson J. B., Moore R. J., ed. Longman House, Essex, GB].

The cosmetically or dermopharmaceutically effective quantity of the exopolysaccharide produced by a strain of *Halomonas anticariensis* species in the composition of the invention to be administered, as well as its dosage, will depend on numerous factors, including age, condition of the patient, the nature or severity of the condition, disorder or disease to be treated and/or cared for, the route and frequency of administration and the nature, in particular, of the exopolysaccharide to be used.

"Cosmetically or dermopharmaceutically effective quantity" is understood to be a non-toxic but sufficient quantity of an ingredient to provide the desired effect. In particular, the exopolysaccharide produced by a strain of *Halomonas anticariensis* species is used at cosmetic or dermopharmaceutic concentrations to achieve the desired effect; in a preferred form, with regard to the total weight of the composition, between 0.0000000001% (in weight) and 20% (in weight); preferably between 0.00000001% (in weight) and 10% (in weight), more preferably between 0.000001% (in weight) and 5% (in weight) and even more preferably between 0.0001% (in weight) and 5% (in weight).

In a particular embodiment, the exopolysaccharide of the invention can also be incorporated into cosmetic or dermopharmaceutical delivery systems and/or sustained release systems.

The term "delivery systems" relates to a diluent, adjuvant, excipient, vehicle or additive with which the exopolysaccharide of the invention is administered. These cosmetic or pharmaceutical carriers can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without limiting sense, liposomes, mixed liposomes, oleosomes, niosomes, ethosomes, milliparticles, microparticles, nanoparticles and solid lipid nanoparticles, nanostructured lipid supports, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as microemulsions and nanoemulsions, which can be added to achieve a greater penetration of the active ingredient and/or to improve the pharmacokinetic and pharmacodynamic properties of it. Preferred delivery or sustained release systems are liposomes, surfactant-phospholipid mixed micelles and microemulsions, more preferably water-in-oil microemulsions with an internal reverse micelle structure and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the compound of the invention. The amount of exopolysaccharide contained in the sustained release system will depend, for example, on where the composition is to be administered, the kinetics and duration of the release of the exopolysaccharide of the invention, as well as the nature of the condition, disorder and/or disease to be treated and/or cared for.

The composition containing the exopolysaccharide of this invention can also be adsorbed on solid organic polymers or solid mineral supports, such as and not restricted to, talc, bentonite, silica, starch or maltodextrin among others.

The compositions containing the exopolysaccharide produced by a strain of *Halomonas anticariensis* species can also be incorporated into fabrics, non-woven fabrics or medical devices which are in direct contact with the skin, thus releasing the exopolysaccharide of the invention whether by biodegradation of the binding system to the fabric, non-woven fabric or medical device, or due to the friction between them and the body, due to body moisture, the skin's pH or body temperature. Furthermore, the exopolysaccharide of the invention can be incorporated into the fabrics and non-woven fabrics used in the manufacture of garments that are in direct contact with the body. Preferably, the fabrics, non-woven fabrics and medical devices containing the compound of the invention are used for the treatment and/or care of conditions, disorders and/or diseases which improve or are prevented by the reduction of the amount of nocturnin, or by stimulation of collagen synthesis.

Examples of fabrics, non-woven fabrics, garments, medical devices and means for immobilizing the compounds to them, among which are the delivery systems and/or the sustained release systems described above, can be found in the literature and are known in the prior art [Schaab C. K. (1986) *HAPPI* May 1986; Nelson G., "*Application of microencapsulation in textiles*", (2002), Int. J. Pharm., 242(1-2), 55-62; "*Biofunctional Textiles and the Skin*" (2006) *Curr. Probl. Dermatol.* v. 33, Hipler U. C. and Elsner P., eds. S. Karger A G, Basel, Switzerland; Malcolm R. K. et al., "*Controlled release of a model antibacterial drug from a novel self-lubricating silicone biomaterial*", (2004), *J. Cont. Release*, 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or dermopharmaceutical compositions containing the exopolysaccharide of this invention can be used in different types of compositions of topical or transdermal application, optionally including cosmetically and/or dermopharmaceutically acceptable excipients necessary for formulating the desired administration form.

The compositions of topical or transdermal application can be produced in any solid, liquid or semi-solid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, liquid crystals, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders, among others.

The cosmetic or dermopharmaceutical compositions of the invention may include agents which increase the percutaneous absorption of the compounds of this invention, for example and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or dermopharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the exopolysaccharide of the invention. The application area will be determined by the nature of the condition, disorder and/or disease to be treated and/or cared for.

Among the cosmetically or dermopharmaceutically acceptable excipients and/or ingredients contained in the cosmetic or dermopharmaceutical compositions described in this invention are additional ingredients commonly used in cosmetic or dermopharmaceutical compositions such as and not restricted to, other agents that reduces the amount of nocturnin, other agents inhibiting the nocturnin expression, lipolytic agents or agents stimulating lipolysis, venotonic agents, agents modulating PGC-1α expression, agents inhibiting the activity of PPARγ, agents which reduce the triglyceride content of adipocytes, anti-cellulite agents, agents delaying adipocyte differentiation, agents which diminish the sebum production, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents which inhibit neuronal exocytosis, anticholinergic agents, agents which inhibit muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor aggregation, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of components of the stratum corneum, ceramides, fatty acids, agents that inhibit collagen degradation, agents that inhibit matrix metalloproteinases, agents that inhibit elastin degradation, agents that inhibit serine proteases such as kallikreins, leukocyte elastase or cathepsin G, agents stimulating fibroblast proliferation, agents stimulating keratinocyte proliferation, agents stimulating melanocyte proliferation, agents stimulating keratinocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, astringent agents, agents which inhibit the activity of PAR-2, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, agents acting on cell metabolism, agents to improve dermal-epidermal junction, agents inducing hair growth, hair growth inhibiting or retardant agents, hair loss retardant agents, preservatives, perfumes, cosmetic and/or absorbent and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided that they are physically and chemically compatible with the rest of components in the composition and particularly with the exopolysaccharide produced by a strain of *Halomonas anticariensis* species. Likewise, the nature of these additional ingredients should not unacceptably alter the benefits of the exopolysaccharide of this invention. The nature of these additional ingredients can be synthetic or natural, such as plant extracts, or come from a biotechnological procedure, or from a combination of a synthetic procedure and a biotechnological procedure. Additional examples can be found in *CTFA International Cosmetic Ingredient Dictionary & Handbook*, 12th Edition (2008). In the context of this invention, biotechnological procedure is understood to be any procedure to produce the active ingredient, or part of it, in an organism, or in part of it.

In one embodiment, the cosmetic and/or dermopharmaceutical composition of the invention contains:

between 0.0000000001% (by weight) and 20% (by weight) of the ferment extract or exopolysaccharide excreted by a strain of *Halomonas anticariensis* species;

between 0.1% (in weight) and 20% (in weight) of an humectant selected from the group of (INCI Names) Glycerin, Propylene Glycol, Butylene Glycol, Pentylene Glycol, Caprylyl Glycol, Lactic Acid, Urea, Sodium Hyaluronate;

between 0.1% (in weight) and 20% (in weight) of an emollient or skin conditioning selected from the group of (INCI Names) Dimethicone, Glyceryl Stearate, Caprylic/Capric Triglyceride, Cetearyl Alcohol, Lecithin, C12-15 Alkyl Benzoate, Squalane, Lanolin, Behenyl Alcohol, Tocopheryl Acetate, Panthenol, *Butyrospermum Parkii* Butter, Retinyl Palmitate, Retinol;

between 0.1% (in weight) and 20% (in weight) of a surfactant selected from the group of (INCI Names) Xanthan Gum, Sodium Laureth Sulfate, Steraric Acid, Polysorbate 20, Polysorbate 80, Stearyl Alcohol, Cetyl Alcohol, Steareth-2, Ceteareth-20, Cocamidopropyl Betaine.

In a particular embodiment, the agent that reduces the triglyceride content of adipocytes, agent that delays adipocyte differentiation, anti-cellulite agent, lipolytic agent, venotonic agent, agent inhibiting PGC-1α expression or agent inhibiting the activity of PPARγ is selected, for example and not restricted to extracts or hydrolyzed extracts of *Alchemilla vulgaris, Angelica sinensis, Armeniacea* sp., *Arnica montana* L, *Atractylodis platicodon*, bamboo, *Betula alba, Bupleurum chinensis, Calendula officinalis*, cangzhu, *Cecropia obtusifolia, Celosia cristata, Centella asiatica, Chenopodium quinoa, Chrysanthellum indicum, Cimifuga racemosa, Citrus aurantium amara, Cnicus benedictus, Coffea arabica, Cola nipida, Coleus barbatus, Coleus blumei, Coleus esquirolii, Coleus forskohlii, Coleus scutellarioides, Coleus* sp., *Coleus xanthanthus, Commiphora myrrha, Crithmum maritimum, Cuminum cyminum, Dioscorea collettii, Dioscorea villosa, Eugenia caryophyllus, Filipendula ulmaria* L, *Foeniculum vulgare, Fucus vesiculosus, Gelidium Cartilagineum, Ginkgo biloba, Ginkgo biloba, Glycine max, Glycyrrhiza glabra, Hedera helix* (ivy extract), *Hibiscus sabdariffa, Hordeum vulgare, Humulus lupulus, Hypericum perforatum, Ilex paraguariensis, Kigelia africana, Laminaria digitata, Lupinus perennis, Nelumbium speciosum, Orthosiphon stamineus benth, Panax ginseng, Paullinia cupana, Peumus boldus*, Phyllacantha fibrosa, *Piper methysticum, Piper nigrum, Prunella vulgaris, Prunus amygdalus dulcis, Rosmarinus officinalis, Rubus idaeus, Ruscus aculeatus* (extract of Butcher's broom), *Salvia officinalis* L, *Sambucus nigra, Serenoa repens, Smilax aristolochiaefolia, Spirulina platensis algae, Taraxacum erythrospermum, Taraxacum officinale*, green tea, *Ulmus rubra, Uncaria tomentosa, Verbena officinalis, Vitex agnus-castus, Dysmorphococcus globosus*, among others, alverin, alverin citrate, dihydromyricetin, coenzyme A, lipase, cerulenin, rutin, glaucine, esculin, visnadine, caffeine, theophylline, theobromine, aminophylline, xanthine, carnitine, forskolin, escin, ruscogenin, hederin, triethanolamine iodide, AMPc synthesis inducing agents, Lanachrys® [INCI: *Chrysanthellum Indicum* Extract] marketed by Atrium/Unipex, Slim-Excess™ [INCI: Water, Butylene Glycol, Sodium Chloride, Hydrolyzed Carrageenan, Xanthan Gum], Sveltine™ [INCI: Water, Butylene Glycol, Carnitine, Lecithin, Caffeine, Carbomer, Salicylic Acid, Atelocollagen, *Centella Asiatica* Extract, Esculin, Sodium Chondroitin Sulfate], Peru Liana [INCI: *Uncaria Tomentosa* Extract] or Flavenger™ [INCI: Caprylic/Capric Triglyceride, Silica Dimethyl Silylate, Glyceryl Oleate, Quercetin Caprylate] marketed by BASF, Scopariane® [INCI: *Sphacelaria Scoparia*], Phyco® R75 [INCI: *Laminaria Digitata*], Pheoslim® [INCI: Phyllacantha Fibrosa Extract], Buckwheat Wax [INCI: *Polygonum fagopyrum*] or Areaumat® Samphira [INCI: *Crithmum Maritimum* Extract], Actiporine™ 8.G [Glycerine, Aqua, *Jania rubens* extract] marketed by Codif, Slimming Factor Karkade™ [INCI: *Hibiscus Sabdariffa*] marketed by Cosmetochem, Liposuctionine™ [proposed INCI: Acetyl Hexapeptide] marketed by Infinitec Activos, Xantalgosil C® [INCI: Acefylline Methylsilanol Mannuronate], Theophyllisilane C® [INCI: Methylsilanol Carboxymethyl Theophylline Alginate], Glutrapeptide® [INCI: Pyroglutamylamidoethyl Indole] or Cafeisilane C® [INCI: Siloxanetriol Alginate, Caffeine, Butylene Glycol] marketed by Exsymol, Timiline® [INCI: Polyglucuronic acid] marketed by Greentech, Visnadine [INCI: Visnadine] or *Ginkgo Biloba* Dimeric Flavonoids Phytosome® [INCI: Phospholipids, *Ginkgo Biloba* Leaf Extract] marketed by Indena, Slimfit® LS 9509 [INCI: *Cecropia Obtusifolia* Bark Extract] marketed by Laboratoires Serobiologiques/Cognis/BASF, Silusyne™ [INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39] or Liporeductyl® [INCI: Water, Glycerin, Lecithin, Caffeine, Butcherbroom (*Ruscus aculeatus*) Root Extract, Maltodextrin, Silica, Tea-Hydroiodide, Propylene Glycol, Ivy (*Hedera Helix*) Extract, Carnitine, Escin, Tripeptide-1, Xanthan Gum, Carrageenan (*Chondrus crispus*), Disodium EDTA] marketed by Lipotec/Lubrizol, Iso-Slim Complex™ [INCI: Soy Isoflavones, Caffeine, Carnitine, *Spirulina Platensis* Extract, Polysorbate 80, Alcohol, Phenoxyethanol, Aqua], Happybelle-PE™ [INCI: Lecithin, *Vitex Agnus Castus* Extract, Glycerin, Ascorbyl Tetraisopalmitate, Tocopherol, Caprylic/Capric Triglyceride, Cyclodextrin, Alcohol, Water] or AmaraShape™ [INCI: Lecithin, Caffeine, *Citrus Aurantium Amara* Extract, Pentylene Glycol, Alcohol, Water] marketed by Mibelle Biochemistry, Regu®-Slim [INCI: Maltodextrin, Caffeine, *Paullinia Cupana* Seed Extract, Carnitine, Microcrystalline Cellulose, Cysteic Acid, Pantheine Sulfonate] or Regu®-Shape [INCI: Isomerized Linoleic Acid, Lecithin, Glycerin, Polysorbate 80] marketed by Pentapharm/DSM, Provislim™ [INCI: Propanediol, Water (Aqua), Fisetin, Raspberry Ketone], Myriceline™ [INCI: Dihydromyricetin] or Drenalip™ [INCI: Ruscus *Aculeatus* Root Extract, *Citrus medica* Limonum Peel Extract, *Solidago virgaurea* Extract, *Astragalus membranaceus* Root Extract] marketed by Provital, Actisculpt® [INCI: *Commiphora Myrrha* Extract, *Coleus Forskohlii* Root Extract] marketed by Givaudan, Perfeline® [INCI: Water, Carnitine, Caffeine, *Ruscus Aculeatus* Extract] or CellActive® Shape [INCI: *Chlorella Vulgaris/Lupinus Albus* Protein Ferment, *Coleus Forskohlii*, Caffeine] marketed by Rahn, ProContour™ [INCI: Water, Alcohol, Lecithin, Caffeine, Carnitine, *Centella Asiatica* Leaf Extract, Potassium Phosphate, *Coleus Forskohlii* Root Extract] marketed by Rovi Cosmetics, Unislim™ [INCI: *Ilex Paraguariensis* (Leaf) Extract, Water, Butylene Glycol, *Coffea Arabica* (Coffee) Seed Extract (Bean), PEG-60 Almond Glycerides, Glycerin, Cetyl Hydroxyethylcellulose], Redulite™ [INCI: Glycerin, Aqua, Ethoxydiglycol, *Sambucus Nigra*, Sodium Polyacrylate], Pleurimincyl™ [INCI: Caffeine, Bupleurum *Chinensis* extract], Phytotal™ SL [INCI: Glycerin, *Verbena Officinalis* Extract, Butylene Glycol, *Sambucus Nigra* Flower Extract, *Eugenia Caryophyllus* (Clove) Flower Extract, Lecithin], Phytosonic™ [INCI: Aqua, *Euglena Gracilis* Extract, Caffeine, *Glaucium Flavum* Leaf Extract], Ovaliss™ [INCI: Glycerin, Aqua, Coco-glucoside, Caprylyl Glycol, Alcohol, Glaucine], Lipocare™ [INCI: Caffeine, Coenzym A, *Bupleurum Chinensis* extract], Cyclolipase™ [INCI: Glyceryl Polymethacrylate, Water, Caffeine, Lipase, Adenosine Phosphate], Coaxel™ [INCI: Caffeine, Coenzyme A, Carnitine, Water, Glycerin], Bodyfit™ [INCI: Glycerin, Aqua (Water), Coco-Glucoside, Caprylyl Glycol, Alcohol, Glaucine] or Vexel® [INCI: Aqua, Propylene glycol, Lecithin, Caffeine, Palmitoyl carnitine] marketed by Sederma/Croda, Voluform® [INCI: Palmitoyl isoleucine], Adipoless™ [INCI: Butylene Glycol, *Chenopodium Quinoa* Seed Extract] marketed by Seppic, Slimactive® [INCI: *Peumus Boldus* Leaf Extract], Remoduline® [INCI: Citrus *Aurantium Amara* Flower Extract], Pro-Sveltyl® [INCI: *Nelumbium Speciosum* Extract], Biosculptine® [INCI: Hydrolyzed *Celosia Cristata* Flower/Seed Extract, Hydrolyzed *Prunella Vulgaris* Extract], Affiness® [INCI: Hydrolyzed *Coriandrum Sativum* Fruit Extract, *Citrus Aurantium Dulcis* (Orange) Fruit Extract] or Stemsvelt® [INCI: Water, Butylene Glycol, *Silybum marinum* extract] marketed by Silab, Delipidol® [INCI: Tyrosyl Punicate], Guaraslim® [INCI: Butylene Glycol, Water, Caffeine, *Paullinia Cupana* Seed Extract, *Ptychopetalum Olacoides* Bark Extract] or Caobromine® [INCI: *Theobroma* Cocoa Shell Extract] marketed by Solabia, Abdoliance™ [INCI: Sucrose palmitate, Polysorbate 20, Glyceryl Linolenate, *Paullinia Cupana* Seed Extract, Maltodextrin, *Prunus Amygdalus Dulcis* (Sweet Almond) Oil, Lecithin, Water, *Citrus Aurantium Amara* (Bitter Orange) Peel Extract, Phenoxyethanol, Tocopherol], Betaphroline [INCI: *Tephrosia Purpurea* Seed Extract] or PRO-DG [INCI: Water, Plankton extract] marketed by Soliance, UCPeptide™ V [INCI: Water, Butylene Glycol, Pentapeptide] or ATPeptide™ IS [INCI: Tripeptide-3] marketed by Vincience/ISP among others, or mixtures thereof.

In a particular embodiment, the firming and/or redensifying and/or restructuring agent is selected, for example and not restricted to, from the group formed by extracts of *Malpighia punicitolia, Cynara scolymus, Gossypium herbaceum, Aloe Barbadensis, Panicum miliaceum, Morus nigra, Sesamum indicum, Glycine soja, Triticum vulgare,* Pronalen® Refirming HSC [INCI: *Triticum Vulgare, Silybum Marianum, Glycine Soy, Equisetum Arvense, Alchemilla Vulgaris, Medicago Sativa, Raphanus Sativus*] or Polyplant® Refirming [INCI: Coneflower, *Asiatic Centella, Fucus,* Fenugreek] marketed by Provital, Lanablue® [INCI: Sorbitol, Algae Extract] marketed by Atrium Biotechnologies/Unipex Innovations, Pepha®-Nutrix [INCI: Natural Nutrition Factor] marketed by Pentapharm/DSM, plant extracts containing isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or BioBustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma/Croda, Dermosaccharides® HC [INCI: Glycerin, Water (Aqua), Glycosaminoglycans, Glycogen], Aglycal® [INCI: Mannitol, Cyclodextrin, Glycogen, *Aratostaphylos Uva Ursi* Leaf Extract], Cytokinol® LS [INCI: Hydrolyzed Casein, Hydrolyzed Yeast Protein, Lysine HCl] or Firmiderm® LS9120 [INCI: *Terminalia Catappa* Leaf Extract, *Sambucus Negra* Flower Extract, PVP, Tannic Acid] marketed by Laboratoires Serobiologiques/Cognis/BASF, Liftline® [INCI: Hydrolyzed Wheat Protein], Raffermine® [INCI: Hydrolyzed Soy Flour] or Ridulisse C® [Hydrolyzed Soy Protein] marketed by Silab, Serilesine® [INCI: Hexapeptide-10], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Silusyne™ [INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39] or Adifyline™ [INCI: Acetyl Hexapeptide-38] marketed by Lipotec/Lubrizol, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/Engelhard/BASF, Syn®-Coll [INCI: Palmitoyl Tripeptide-5] marketed by Pentapharm/DSM, Hydriame® [INCI: Water (Aqua), Glycosaminoglycans, Sclerotium Gum] marketed by Atrium Biotechnologies/Unipex Innovations or IP2000™ [INCI: Dextran, Trifluoroacetyl Tripeptide-2] marketed by Institut Europeen de Biologie Cellulaire/Unipex Innovations, among others.

In a particular embodiment, the agent stimulating the synthesis of dermal or epidermal macromolecules is selected, for example and not restricted to, from the group formed by collagen synthesis-stimulating agents, elastin synthesis-stimulating agents, decorin synthesis-stimulating agents, laminin synthesis-stimulating agents, chaperone synthesis-stimulating agents, sirtuin synthesis-stimulating agents, sirtuin activating agents, aquaporin synthesis-modulating agents, fibronectin synthesis-stimulating agent, agents that inhibit collagen degradation, agents that inhibit elastin degradation, agents that inhibit serine proteases such as kallikreins, leukocyte elastase or cathepsin G, agents stimulating fibroblast proliferation, and DNA repairing agents and/or DNA protecting agents, such as and not restricted to extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of soy, malt, flax, sage, red clover, kakkon, white lupin plants, hazelnut extract, maize extract, yeast extract, beech shoot extracts, leguminous seed extract, plant hormone extract such as gibberellins, auxins or cytokinins, among others, or extract of zooplankton Salina, the fermentation product of milk with *Lactobacillus Bulgaricus*, asiaticosides and their derivatives, vitamin C and its derivatives, cinnamic acid and its derivatives, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma/Croda, Antarcticine® [INCI: Pseudoalteromonas Ferment Extract], Decorinyl® [INCI: Tripeptide-10 Citrulline], Serilesine® [INCI: Hexapeptide-10], Lipeptide® [INCI: Hydrolyzed Vegetable Protein], Aldenine® [INCI: Hydrolyzed Wheat Protein, Hydrolyzed Soy Protein, Tripeptide-1], Relistase™ [INCI: Acetylarginyltriptophyl Diphenylglycine], Thermostressine™ [INCI: Acetyl Tetrapeptide-22], Peptide AC29 [INCI: Acetyl Tripeptide-30 Citrulline], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline™ [INCI: Acetyl Hexapeptide-38] marketed by Lipotec/Lubrizol, Drieline® PF [INCI: Yeast Betaglucan] marketed by Alban Muller, Phytovityl C® [INCI: Aqua, *Zea Mays* Extract] marketed by Solabia, Collalift® [INCI: Hydrolyzed Malt Extract] marketed by Coletica/Engelhard/BASF, Phytocohesine PSP™ [INCI: Sodium Beta-Sitosterol Sulfate] marketed by Vincience/ISP/Ashland, minerals such as calcium, among others, retinoids and their derivatives, isoflavonoids, carotenoids, in particular lycopene, pseudodipeptides, retinoids and their derivatives such as retinol or retinyl palmitate, among others, or heparinoids, among others.

In a particular embodiment, the anti-wrinkle and/or anti-aging agent is selected, for example and not restricted to, from the group formed by the extracts or hydrolyzed extracts of *Vitis vinifera, Rosa canina, Curcuma longa, Theobroma cacao, Ginkgo biloba, Leontopodium alpinum* or *Dunaliella salina* among others, Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6™ [INCI: Glycerin, Water, Hydroxypropyl Cyclodextrin, Palmitoyl Tripeptide-38], Essenskin™ [INCI: calcium hydroxymethionine], Renovage™ [INCI: teprenone], Resistem™ [INCI: *Globularia Cordifolia* Ferment] or Dermaxyl® [INCI: Palmitoyl Oligopeptide] marketed by Sederma/Croda, Vialox® [INCI: Pentapeptide-3], Syn® Ake® [INCI: Dipeptide Diaminobutyroyl Benzylamide Diacetate], Syn®-Coll [INCI: Palmitoyl Tripeptide-5], Phytaluronate® [INCI: Locust Bean (*Ceratonia siliqua*) Gum] or Preregen® [INCI: *Glycine soja* (Soybean) Protein, Oxido Reductases] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9] or DN AGE™ LS [INCI: *Cassia alata* leaf Extract] marketed by Laboratoires Sérobiologiques/Cognis/BASF, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7™ [INCI: Acetyl Heptapeptide-4], SNAP-8™ [INCI: Acetyl Octapeptide-3], Leuphasyl® [INCI: Pentapeptide-18], Inyline™ [INCI: Acetyl Hexapeptide-30], Aldenine® [INCI: Hydrolyzed Wheat Protein, Hydrolyzed Soy Protein, Tripeptide-1], Preventhelia™ [INCI: Diaminopropionoyl Tripeptide-33], Decorinyl® [INCI: Tripeptide-10 Citrulline], Decorinol® [INCI: Tripeptide-9 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase™ [INCI: Acetylarginyltriptophyl Diphenylglycine], Thermostressine® [INCI: Acetyl Tetrapeptide-22], Lipochroman™ [INCI: Dimethylmethoxy Chromanol], Chromabright™ [INCI: Dimethylmethoxy Chromanyl Palmitate], Antarcticine® [INCI: *Pseudoalteromonas* Ferment Extract], dGlyage™ [INCI: Lysine HCl, Lecithin, Tripeptide-9 Citrulline], Vilastene™ [INCI: Lysine HCl, Lecithin, Tripeptide-10 Citrulline], Hyadisine™ [INCI: *Pseudoalteromonas* Ferment Extract], Hyanify™ [INCI: Saccharide Isomerate], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39], Adifyline™ [INCI: Acetyl Hexapeptide-38] Uplevity™ [INCI: Acetyl Tetrapeptide-2] or Juvefoxo™ [INCI: Acetyl Hexapeptide-51 amide] marketed by Lipotec/Lubrizol, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract] or Quintescine™ IS [INCI: Dipeptide-4] marketed by Vincience/ISP/Ashland, BONT-L-Peptide™ [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen®4 [INCI: Acetyl Tetrapeptide-2] marketed by Atrium/Unipex Innovations, EquiStat™ [INCI: *Pyrus malus* Fruit Extract, *Glycine soja* Seed Extract] or Juvenesce™ [INCI: Ethoxydiglicol and Caprylic Triglyceride, Retinol, Ursolic Acid, Phytonadione, Ilomastat] marketed by Coletica/Engelhard/BASF, Ameliox™ [INCI: Carnosine, Tocopherol, *Silybum marianum* Fruit Extract] or PhytoCellTec *Malus Domestica* [INCI: *Malus domestica* Fruit Cell Culture] marketed by Mibelle Biochemistry, Bioxilift™ [INCI: *Pimpinella anisum* Extract] or SMS Anti-Wrinkle® [INCI: *Annona squamosa* Seed Extract] marketed by Silab, antagonists of the $Ca^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes such as and not restricted to, photolyase or T4 endonuclease V, or chloride channel agonists among others, and/or mixtures thereof.

In another particular embodiment, then anti-inflammatory agent and/or analgesic is selected, for example and not restricted to, from the group formed by extract of madecassoside, extract of echinacea, amaranth seed oil, sandal wood oil, extract of peach tree leaf, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca aftemifolia, Origanum majorana, Origanum vulgare, Prunus laurocerasus, Rosmarinus officinalis, Salix alba, Silybum marianum, Tanacetum parthenium, Thymus vulgaris, Uncaria guianensis* or *Vaccinium myrtillus*, omega-3 and omega-6 fatty acids, Neutrazen™ [INCI: Water, Butylene Glycol, Dextran, Palmitoyl Tripeptide-8] marketed by Atrium Innovations/Unipex Group, Delisens™ [proposed INCI: Acetyl Hexapeptide-46] marketed by Lipotec/Lubrizol, Meliprene® [INCI: Dextran, Acetyl Heptapeptide-1] marketed by Institut Europeen de Biologie Cellulaire/Unipex Group, Skinasensyl™ [INCI: Acetyl Tetrapeptide-15] or Anasensyl™ [INCI: Mannitol, Ammonium Glycyrrhizate, Caffeine, *Hippocastanum* (Horse Chestnut) Extract] marketed by Laboratoires Serobiologiques/Cognis/BASF, Calmosensine™ [INCI: Acetyl Dipeptide-1] marketed by Sederma/Croda, coenzyme Q10 or alkyl glyceryl ethers, among others, or mixtures thereof.

Applications

In another aspect this invention refers to the use of the exopolysaccharide produced by a strain of *Halomonas anticariensis* species in the preparation of a cosmetic or dermopharmaceutical composition for the treatment and/or care of the skin. In particular, the treatment and/or care refers to the treatment of inflammation in the skin, treatment of re-epithelialization and/or wound healing of the skin, treatment and/or prevention of cellulite, treatment of reduction of lipid accumulation in the skin, treatment of stimulation of lipolysis in the skin, treatment of stimulation of collagen synthesis, treatment and/or prevention of skin aging, treatment and/or prevention of skin wrinkles, treatment for improving skin firmness, for prevention of loss of skin firmness and/or treatment for improving skin elasticity. In particular the inflammation is selected, for example and not restricted to, from the group formed by psoriasis, sensitive skin, dermatitis, atopic dermatitis, contact dermatitis, diaper dermatitis, seborrheic dermatitis, eczema, rosacea, acne, hyperproliferative skin disease, burns, sunburn, paronychia, skin inflammation after surgery, after treatment with intense pulsed light therapy (IPL), after treatment with monochromatic pulsed light therapy (laser), after treatment with chemical peeling agents or after overexposure to aggressive external agents, among others. In particular, the strain of *Halomonas anticariensis* species is a strain of *Halomonas anticariensis* species with deposit number LMG P-27891.

In another particular embodiment, this invention refers to the use of the exopolysaccharide produced by a strain of *Halomonas anticariensis* species in the preparation of a cosmetic or dermopharmaceutical composition for the reduction of the amount of nocturnin in the cells. In particular, the strain of *Halomonas anticariensis* species is a strain of *Halomonas anticariensis* species with deposit number LMG P-27891.

An additional aspect of this invention refers to a method of treatment and/or care of the skin which comprises the administration of a cosmetically or dermopharmaceutically effective quantity of the exopolysaccharide produced by a strain of *Halomonas anticariensis* species. In particular, the treatment and/or care refers to the treatment of inflammation in the skin, treatment of re-epithelialization and/or wound healing of the skin, treatment and/or prevention of cellulite, treatment of reduction of lipid accumulation in the skin, treatment of stimulation of lipolysis in the skin, treatment and/or prevention of skin aging, treatment and/or prevention of skin wrinkles, treatment for improving skin firmness, for prevention of loss of skin firmness and/or treatment for improving skin elasticity. In particular the inflammation is selected, for example and not restricted to, from the group formed by psoriasis, sensitive skin, dermatitis, atopic dermatitis, contact dermatitis, diaper dermatitis, seborrheic dermatitis, eczema, rosacea, acne, hyperproliferative skin disease, burns, sunburn, paronychia, skin inflammation after surgery, after treatment with intense pulsed light therapy (IPL), after treatment with monochromatic pulsed light therapy (laser), after treatment with chemical peeling agents or after overexposure to aggressive external agents, among others. In particular, the strain of *Halomonas anticariensis* species is a strain of *Halomonas anticariensis* species with deposit number LMG P-27891.

In another particular embodiment, this invention refers to a method of reduction of the amount of nocturnin in the cells which comprises the administration of a cosmetically or pharmaceutically effective quantity of the exopolysaccharide produced by a strain of *Halomonas anticariensis* species. In particular, the strain of *Halomonas anticariensis* species is a strain of *Halomonas anticariensis* species with deposit number LMG P-27891.

In another aspect, the exopolysaccharide produced by a strain of *Halomonas anticariensis* species can be administered by any means that causes its contact with the site of action in a mammal's body, preferably that of a human being, and more preferably, in the form of a composition which contains it. The administration of the exopolysaccharide produced by a strain of *Halomonas anticariensis* species is carried out topically or transdermally. In a more particular aspect topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The frequency of the application or administration can vary widely, depending on the needs of each subject, suggesting a range of application or administration from once per month to 10 times per day, preferably from once per week to 4 times per day, more preferably from three times per week to three times per day, even more preferably once per day.

Deposit of Biological Material

The strain of the *Halomonas anticariensis* species was deposited at the Belgian Coordinated Collection of Microorganisms (BCCM)/Laboratorium voor Microbiologie-Bacteriëverzameling (LMG) (University Ghent, K. L. Ledeganckstraat 35, 9000 Ghent, Belgium) under the conditions of the Budapest Treaty. The deposit was done on Sep. 18, 2013 and the deposit number was LMG P-27891.

EXAMPLES

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as approximated, i.e., subject to a variability of ±5%, more preferably of ±3%, more preferably of ±1%, more preferably of ±0.1%, even more preferably of ±0.01% over the indicated value.

Example 1: Obtaining the Exopolysaccharide Secreted by the Strain of the *Halomonas anticariensis* Species with Deposit Number LMG P-27891

A) Culture Process of the Strain of the *Halomonas anticariensis* Species with Deposit Number LMG P-27891.

The strain of the *Halomonas anticariensis* species with deposit number LMG P-27891 is cultivated in a fermenter, at 32° C. and at a pH of 7.0, in a culture medium containing water, 10 g/L of glucose as source of carbon, 3 g/L of yeast extract and 3 g/L of malt extract as sources of carbon and nitrogen, and a salt solution containing NaCl, magnesium, calcium, potassium and bicarbonate salts. It is inoculated at a 520 nm absorbance of 0.2 UA, absorbance units, from a pre-culture in an exponential state of growth and the fermentation duration is extended to 44 hours of culture. The dissolved oxygen concentration is controlled at 30% saturated air and the stirring is maintained at values between 300 and 650 rpm.

B) Purification of the Exopolysaccharide of the Strain of the *Halomonas anticariensis* Species Deposited Under Deposit Number LMG P-27891.

The bacteria is separated from the resulting fermentation broth described in example 1a) containing the exopolysaccharide by centrifugation at 6,000 g for 1 hour. The removal of the bacteria is completed by filtration at a final pore size of 0.65 µm and the subsequent freeze-drying of the resulting supernatant containing the exopolysaccharide.

Example 2: Physicochemical Characterization of the Exopolysaccharide Excreted by the Strain of the *Halomonas anticariensis* Species with Deposit Number LMG P-27891

A high performance liquid chromatography (HPLC) and infrared spectroscopy (IR) analysis (refractive index detector) has been performed for the physicochemical characterization of the exopolysaccharide produced by the strain of the *Halomonas anticariensis* species with deposit number LMG P-27891 and on the monosaccharide content of the exopolysaccharide obtained in accordance with example 1.

High Performance Liquid Chromatography (HPLC) and Infrared Spectroscopy (IR) Analysis In order to carry out the HPLC-IR chromatograms, samples are prepared from the exopolysaccharide obtained in accordance with example 1 b) diluting them in water at 3 mg/mL and filtering them with 0.22 µm polyethersulfone filters. The HPLC analysis is carried out using 100 µL injection of the sample on an LC20A™ SHIMADZU chromatography equipment. The chromatographic column used is PL AQUAGEL-OH™ 8 µm AQUEOUS SEC COLUMNS, and the detector, RID-10A Refractive Index Detector (Shimadzu). The solvent used is 0.1 M sodium acetate in water and flow rate 0.8 ml/min. PL AQUAGEL-OH™ 8 µm AQUEOUS SEC COLUMNS is a column for aqueous Size Exclusion Chromatography, with a packaging having the capacity to separate compounds depending on its MW, applied to neutral, anionic and cationic water-soluble polymers and with a particle size of 8 µm, a pore size of 50 Å and a length/Internal Diameter of 300 mm×7.5 mm.

The result of the analysis shows a peak with a center at 5.9 mins for the exopolysaccharide and the fraction is gathered with a retention time of between 5 and 8 minutes.

Analysis of Monosaccharides

The exopolysaccharide obtained in accordance with example 1 is dialyzed with a 300 KDa polyethersulfone membrane for distilled water. The exopolysaccharide retained by the membrane is subsequently freeze-dried. In order to perform the monosaccharide analysis from the solid, the method described by Kamerling et al., *Biochem. J.*, 1975 151, 491-495 as later modified by Montreuil et al. in, *Glycoproteins. In Carbohydrate analysis: a practical approach*, 1986, Eds Chaplin and Kennedy, I.R.L Press, Oxford, Washington D.C., 143-204 is followed. The derivatization of the hydrolyzed monosaccharides is carried out according to literature methods Rojas Escudero et al., *J. Chromatogr. A.*, 2004, 1027:117-120. A ZEBRON ZB-1701™ (Phenomenex) column, an injector temperature of 250° C., a detector temperature of 280° C., and oven temperature ramp programming of 160° C. to 250° C. are used for the chromatographic analysis.

As a result of this analysis, the percentages of monosaccharides obtained are 15.21% of glucose, 59.95% of mannose, 24.07% of rhamnose, 0.30% of xylose and 0.47% of galacturonic acid.

Example 3: Preparation of a Cosmetic Cream Composition Comprising the Exopolysaccharide of the Strain of the *Halomonas anticariensis* Species with Deposit Number LMG P-27891

In an appropriate container, water [INCI: WATER (AQUA)], Hydrolite-5® 2/016020 [INCI: PENTYLENE GLYCOL], Microcare BNA [INCI: BENZYL ALCOHOL], Carbopol® Ultrez 10 [INCI: CARBOMER], and Arlatone® MAP 160K [INCI: POTASSIUM CETYL PHOSPHATE] are mixed. This mixture of ingredients is constantly stirred and heated to 70-75° C. This mixture of ingredients constitutes phase A.

In another container, the phase B ingredients, ethylhexyl cocoate [INCI: ETHYLHEXYL COCOATE], Phytocream® 2000 [INCI: GLYCERYL STEARATE, CETEARYL ALCOHOL, POTASSIUM PALMITOYL HYDROLYZED WHEAT PROTEIN], Finsolv® TN [INCI: C12-15 ALKYL BENZOATE], DC200 Silicone [INCI: DIMETHICONE] and phenoxyethanol [INCI: PHENOXYETHANOL] are also dissolved at 70-75° C. Once dissolved, they are slowly added to phase A under turbine stirred.

Phase C included the exopolysaccharide of the strain of the *Halomonas anticariensis* species with deposit number LMG P-27891 of example 1, together with water [INCI: WATER (AQUA)], disodium hydrogenphosphate 12-hydrate [INCI: DISODIUM PHOSPHATE], sodium dihydrogenphosphate 2-hydrate [INCI: SODIUM PHOSPHATE], ZEMEA® propanediol [INCI: PROPANEDIOL], Dermosoft® GMCY [INCI: GLYCERYL CAPRYLATE] and xanthan gum [INCI: XANTHAN GUM], which is added to the mixture of ingredients of phases A and B at 40° C., under stirring.

Then, under rotor stirring, Sepigel™ 305 [INCI: WATER (AQUA), POLYACRYLAMIDE, C13-14 ISOPARAFFIN, LAURETH-7] (phase D) is added to the resulting emulsion of the mixture of the different phases.

Immediately, the fragrance Tonus E20040401 [INCI: FRAGRANCE (PARFUM)] (Phase E) is added to the mixture, again under rotor stirring.

The pH is adjusted to 6.0-6.5 by addition of sodium hydroxide [INCI: SODIUM HYDROXIDE] (q.s. sufficient quantity to adjust to this pH) under stirring (phase F), obtaining a cosmetic composition with the proportions shown in table 1.

TABLE 1

|   | INGREDIENT | % weight |
|---|---|---|
| A | WATER (AQUA) | 79.20 |
| A | PENTYLENE GLYCOL | 5.00 |
| A | BENZYL ALCOHOL | 0.40 |
| A | CARBOMER | 0.50 |
| A | POTASSIUM CETYL PHOSPHATE | 0.50 |
| B | ETHYLHEXYL COCOATE | 2.50 |
| B | GLYCERYL STEARATE | 2.05 |
| B | CETEARYL ALCOHOL | 2.05 |
| B | POTASSIUM PALMITOYL HYDROLYZED WHEAT PROTEIN | 0.90 |
| B | C12-15 ALKYL BENZOATE | 2.00 |
| B | DIMETHICONE | 1.00 |
| B | PHENOXYETHANOL | 0.80 |
| C | WATER (AQUA) | 1.42 |
| C | PROPANEDIOL | 0.49 |
| C | DISODIUM PHOSPHATE | 0.03 |
| C | XANTHAN GUM | 0.02 |
| C | SODIUM PHOSPHATE | 0.02 |
| C | GLYCERYL CAPRYLATE | 0.01 |
| C | Exopolysaccharide from example 1 | 0.01 |
| D | POLYACRYLAMIDE | 0.40 |
| D | WATER (AQUA) | 0.34 |
| D | C13-14 ISOPARAFFIN | 0.20 |
| D | LAURETH-7 | 0.06 |
| E | FRAGRANCE (PARFUM) | 0.10 |
| F | SODIUM HYDROXIDE 20% | q.s. |

Example 4: Preparation of a Cosmetic Light Cream Composition Comprising the Exopolysaccharide of the Strain of the *Halomonas anticariensis* Species with Deposit Number LMG P-27891

In an appropriate container, water [INCI: WATER (AQUA)], Hydrolite-5® 2/016020 [INCI: PENTYLENE GLYCOL], propylene glycol [INCI: PROPYLENE GLYCOL], Microcare® BNA [INCI: BENZYL ALCOHOL], and Carbopol® ETD 2020 [INCI: ACRYLATES/C10-30 ALKYL ACRYLATE CROSSPOLYMER] are mixed. This mixture of ingredients is constantly stirred until they dissolved, and is heated to 70-75° C. This mixture of ingredients constitutes phase A.

In another container, the phase B ingredients, caprylic/capric triglycerides [INCI: CAPRYLIC CAPRIC TRIGLYCERIDE], phenoxyethanol [PHENOXYETHANOL], stearic acid [INCI: STEARIC ACID], palmitic acid [INCI: PALMITIC ACID], cetyl alcohol [INCI: CETYL ALCOHOL], Massocare™ HD [INCI: ISOHEXADECANE], Arlacel™ 165 (Lipomulse) [INCI: GLYCERYL STEARATE, PEG-100 STEARATE], are also dissolved at 70-75° C.

Phase C includes the exopolysaccharide of the strain of *Halomonas anticariensis* species with deposit number LMG P-27891 of example 1, together with water [INCI: WATER (AQUA)], disodium hydrogenphosphate 12-hydrate [INCI: DISODIUM PHOSPHATE], sodium dihydrogenphosphate 2-hydrate [INCI: SODIUM PHOSPHATE], ZEMEA® propanediol [INCI: PROPANEDIOL], Dermosoft® GMCY [INCI: GLYCERYL CAPRYLATE] and xanthan gum [INCI: XANTHAN GUM], and it is added to the mixture of ingredients of phases A and B at 40° C., under stirring.

Then, under rotor stirring the phase D components, Sepigel™ 305 [INCI: POLYACRYLAMIDE, WATER (AQUA), C13-14 ISOPARAFFIN, LAURETH-7] and the fragrance tonus E20040401 [INCI: FRAGRANCE (PARFUM)] are added to the mixture.

The pH is adjusted to 6.0-6.5 by addition of sodium hydroxide [INCI: SODIUM HYDROXIDE] (q.s. sufficient quantity to adjust to this pH) under stirring (phase E), obtaining a cosmetic composition with the proportions shown in table 2.

TABLE 2

|   | INGREDIENT | % weight |
|---|---|---|
| A | WATER (AQUA) | 69.05 |
| A | PENTYLENE GLYCOL | 5.00 |
| A | PROPYLENE GLYCOL | 2.00 |
| A | BENZYL ALCOHOL | 0.40 |
| A | ACRYLATES/C10-30 ALKYL ACRYLATE CROSSPOLYMER | 0.15 |
| B | CAPRYLIC CAPRIC TRIGLYCERIDE | 8.00 |
| B | PHENOXYETHANOL | 0.80 |
| B | STEARIC ACID | 0.90 |
| B | PALMITIC ACID | 0.90 |
| B | CETYL ALCOHOL | 0.70 |
| B | ISOHEXADECANE | 3.00 |
| B | GLYCERYL STEARATE | 3.00 |
| B | PEG-100 STEARATE | 3.00 |
| C | WATER (AQUA) | 1.42 |
| C | PROPANEDIOL | 0.49 |
| C | DISODIUM PHOSPHATE | 0.03 |
| C | XANTHAN GUM | 0.02 |
| C | SODIUM PHOSPHATE | 0.02 |
| C | GLYCERYL CAPRYLATE | 0.01 |
| C | Exopolysaccharide from example 1 | 0.01 |
| D | POLYACRYLAMIDE | 0.40 |
| D | WATER (AQUA) | 0.34 |
| D | C13-14 ISOPARAFFIN | 0.20 |
| D | LAURETH-7 | 0.06 |
| D | FRAGRANCE (PARFUM) | 0.10 |
| E | SODIUM HYDROXIDE 20% | q.s. |

Example 5: Preparation of a Cosmetic Gel Cream Composition Comprising the Exopolysaccharide of the Strain of the *Halomonas anticariensis* Species with Deposit Number LMG P-27891

In an appropriate container, water [INCI: WATER (AQUA)], Hydrolite-5® 2/016020 [INCI: PENTYLENE GLYCOL], glycerine [INCI: GLYCERIN], Betafin® BP [INCI: BETAINE], and Carbopol® Ultrez 10 [INCI: CARBOMER] are mixed under stirring. Then, Arlatone® Map 160 K [INCI: POTASSIUM CETYL PHOSPHATE] is added until dispersion and the entire mixture is heated at 70-50° C. This mixture of ingredients constitutes phase A.

In another container, the phase B ingredients, Massocare™ HD [INCI: ISOHEXADECANE], Finsolv® TN [INCI: C12-C15 ALKYL BENZOATE], cetyl alcohol [INCI: CETYL ALCOHOL], phenoxyethanol [PHENOXYETHANOL], Polysorbate 20 [INCI: POLYSORBATE 20], stearic acid [INCI: STEARIC ACID], palmitic acid [INCI: PALMITIC ACID] and vitamin E acetate [INCI: TOCOPHERYL ACETATE] are also dissolved at 70-75° C., and slowly added to phase A under turbine stirring.

Phase C includes the exopolysaccharide of the strain of the *Halomonas anticariensis* species with deposit number LMG P-27891 of example 1, together with water [INCI: WATER (AQUA)], disodium hydrogenphosphate 12-hydrate [INCI: DISODIUM PHOSPHATE], sodium dihydrogenphosphate 2-hydrate [INCI: SODIUM PHOSPHATE], ZEMEA® propanediol [INCI: PROPANEDIOL], Dermosoft® GMCY [INCI: GLYCERYL CAPRYLATE] and xanthan gum [INCI: XANTHAN GUM], and it is added to the mixture of ingredients of phases A and B at 40° C., under stirring.

Then, the only phase D component, the fragrance tonus E20040401 [INCI: FRAGRANCE (PARFUM)] is added, under rotor stirring, to the previous mixture until homogenization.

The pH is adjusted to 6.0-6.5 by addition of sodium hydroxide [INCI: SODIUM HYDROXIDE] (q.s sufficient quantity to adjust to this pH) under stirring (phase E), obtaining a cosmetic composition with the proportions shown in table 3.

TABLE 3

| | INGREDIENT | % weight |
|---|---|---|
| A | WATER (AQUA) | 75.25 |
| A | PENTYLENE GLYCOL | 5.00 |
| A | GLYCERIN | 3.00 |
| A | BETAINE | 3.00 |
| A | CARBOMER | 0.35 |
| A | POTASSIUM CETYL PHOSPHATE | 0.40 |
| B | ISOHEXADECANE | 2.00 |
| B | C12-C15 ALKYL BENZOATE | 2.00 |
| B | CETYL ALCOHOL | 1.80 |
| B | PHENOXYETHANOL | 0.90 |
| B | POLYSORBATE 20 | 0.80 |
| B | STEARIC ACID | 0.25 |
| B | PALMITIC ACID | 0.25 |
| B | TOCOPHERYL ACETATE | 0.50 |
| C | WATER (AQUA) | 1.42 |
| C | PROPANEDIOL | 0.49 |
| C | DISODIUM PHOSPHATE | 0.03 |
| C | XANTHAN GUM | 0.02 |
| C | SODIUM PHOSPHATE | 0.02 |
| C | GLYCERYL CAPRYLATE | 0.01 |
| C | Exopolysaccharide from example 1 | 0.01 |
| C | CYCLOMETHICONE | 2.00 |
| D | FRAGRANCE (PARFUM) | 0.10 |
| E | SODIUM HYDROXIDE 20% | q.s. |

Example 6: Preparation of a Microemulsion Comprising the Exopolysaccharide of the Strain of the *Halomonas anticariensis* Species with Deposit Number LMG P-27891

In an appropriate container, Docusate Sodium USP [INCI: DIETHYLHEXYL SODIUM SULFOSUCCINATE] and isostearic acid [INCI: ISOSTEARIC ACID] are mixed (phase A).

In another container, a mixture of the exopolysaccharide of the strain of *Halomonas anticariensis* species with deposit number LMG P-27891 of example 1, together with water [INCI: WATER (AQUA)], disodium hydrogenphosphate 12-hydrate [INCI: DISODIUM PHOSPHATE], sodium dihydrogenphosphate 2-hydrate [INCI: SODIUM PHOSPHATE], ZEMEA® propanediol [INCI: PROPANEDIOL], Dermosoft® GMCY [INCI: GLYCERYL CAPRYLATE] and xanthan gum [INCI: XANTHAN GUM] is dissolved in ethanol [INCI: ALCOHOL] (phase B). Slowly, phase B is added to phase A under stirring. See table 4.

TABLE 4

| | INGREDIENT | % weight |
|---|---|---|
| A | DIETHYLHEXYL SODIUM SULFOSUCCINATE | 15.00 |
| A | ISOSTEARIC ACID | 75.00 |
| B | AQUA | 4.98 |
| B | PROPANEDIOL | 1.72 |
| B | DISODIUM PHOSPHATE | 0.10 |
| B | XANTHAN GUM | 0.07 |
| B | SODIUM PHOSPHATE | 0.06 |
| B | GLYCERYL CAPRYLATE | 0.04 |
| B | Exopolysaccharide from example 1 | 0.04 |
| B | ALCOHOL | 3.00 |

Example 7: Preparation of a Lipid Nanoparticle Composition Comprising the Microemulsion of Example 6

Water [INCI: WATER (AQUA)], Amigel® [INCI: *SCLEROTIUM* GUM], Zemea™ [INCI: PROPANEDIOL] and phenoxyethanol [INCI: PHENOXYETHANOL] (phase A ingredients) are added in that order to an appropriate container and stirred until homogeneity is achieved.

The mixture comprising the microemulsion of example 6, refined soybean oil IP Ph. Eur. [INCI: *GLYCINE SOJA* (SOYBEAN) OIL], Arlacel™ 83V [INCI: SORBITAN SESQUIOLEATE], and Arlamol™ HD [INCI: ISOHEXADECANE] (phase B ingredients) is added to another container.

Then, the mixture of the phase B ingredients is added to the mixture of the phase A ingredients under turbine stirring until an emulsion is formed.

Finally, the mixture is homogenized with a titanium probe for one minute.

Then, dropwise and under stirring, a water [INCI: WATER (AQUA)] suspension of SENSOMER™ CT-400 [INCI: CASSIA HYDROXYPROPYLTRIMONIUM CHLORIDE] is added (phase C INGREDIENTS). See table 5.

TABLE 5

| | INGREDIENT | % WEIGHT |
|---|---|---|
| A | WATER (AQUA) | q.s. 100 |
| A | *SCLEROTIUM* GUM | 0.50 |
| A | PROPANEDIOL | 5.00 |
| A | PHENOXYETHANOL | 2.6 |
| B | Microemulsion of example 6 | 8.00 |
| B | GLYCINE SOJA (SOYBEAN) OIL | 12.00 |
| B | SORBITAN SESQUIOLEATE | 4.30 |
| B | ISOHEXADECANE | 5.50 |
| C | WATER (AQUA) | 2.00 |
| C | CASSIA HYDROXYPROPYLTRIMONIUM CHLORIDE | 0.20 |

Example 8: Obtaining Liposomes Comprising the Exopolysaccharide of the Strain of the *Halomonas anticariensis* Species with Deposit Number LMG P-27891

A mixture of the exopolysaccharide of the strain of *Halomonas anticariensis* species with deposit number LMG P-27891 of example 1 is placed into an appropriate container, together with water [INCI: WATER (AQUA)], disodium hydrogenphosphate 12-hydrate [INCI: DISODIUM PHOSPHATE], sodium dihydrogenphosphate 2-hydrate [INCI: SODIUM PHOSPHATE], ZEMEA® propanediol

[INCI: PROPANEDIOL], Dermosoft® GMCY [INCI: GLYCERYL CAPRYLATE] and xanthan gum [INCI: XANTHAN GUM] (phase A). Water, Zemea™ [INCI: PROPANEDIOL] and phenoxyethanol [INCI: PHENOXYETHANOL] (phases B to D) are added to this phase. When all the previous components are dissolved, Leciflor 100 IP™ [INCI: LECITHIN] (phase E) is added little by little and under intense stirring, until completely dissolved. Then, Labrasol® [INCI: PEG-8 CAPRYLIC/CAPRIC GLYCERIDES] (phase F) is added and left to stir for 15 minutes to form an emulsion. The final obtained composition is shown in table 6.

TABLE 6

|   | INGREDIENT | % weight |
|---|---|---|
| A | WATER (AQUA) | 7.11 |
| A | PROPANEDIOL | 2.45 |
| A | DISODIUM PHOSPHATE | 0.15 |
| A | XANTHAN GUM | 0.10 |
| A | SODIUM PHOSPHATE | 0.09 |
| A | GLYCERYL CAPRYLATE | 0.05 |
| A | Exopolysaccharide from example 1 | 0.05 |
| B | WATER (AQUA) | q.s. 100 |
| C | PROPANEDIOL | 8.50 |
| D | PHENOXYETHANOL | 1.70 |
| E | LECITHIN | 10.00 |
| F | PEG-8 CAPRYLIC/CAPRIC GLYCERIDES | 4.00 |

The sample is homogenized with a titanium probe for 30 seconds.

Example 9: Obtaining Liposomes of Example 8 Bound to Cationic Polymers

The liposomes obtained in example 8 are added to SENSOMER® CT-50 [INCI: WATER (AQUA), STARCH HYDROXYPROPYLTRIMONIUM CHLORIDE, UREA, SODIUM LACTATE, SODIUM CHLORIDE, SODIUM BENZOATE] at a liposomes/cationic polymer ratio of 95:5 under slow stirring.

Example 10: Preparation of a Cosmetic Composition Comprising Lipid Nanoparticles of Example 7

In an appropriate container water [INCI: WATER (AQUA)], Hydrolite-5® 2/016020 [INCI: PENTYLENE GLYCOL], Microcare® BNA [INCI: BENZYL ALCOHOL], and Carbopol® Ultrez 10 [INCI: CARBOMER], are mixed under stirring. Next, Arlatone® Map 160 K [INCI: POTASSIUM CETYL PHOSPHATE] is added until dispersed and the entire mixture is heated at 70-50° C. This mixture of ingredients constitutes phase A.

In another container, the phase B ingredients ethylhexyl cocoate [INCI: ETHYLHEXYL COCOATE], Phytocream 2000 [INCI: GLYCERYL STEARATE, CETEARYL ALCOHOL, POTASSIUM PALMITOYL HYDROLYZED WHEAT PROTEIN], Finsolv® TN [INCI: C12-15 ALKYL BENZOATE], DC200 Silicone [INCI: DIMETHICONE] and phenoxyethanol [INCI: PHENOXYETHANOL] are also dissolved at 70-75° C. Once dissolved, they are added slowly to phase A under turbine stirring.

Phase C, the composition of example 7, is added to the mixture of the phases A and B ingredients at 40° C., under stirring.

Then, the phase D component, Sepigel™ 305 [INCI: POLYACRYLAMIDE, WATER (AQUA), C13-C14 ISOPARAFFIN, LAURETH-7], and phase E, the fragrance tonus E20040401 [INCI: FRAGRANCE (PARFUM)], are added to the mixture under rotor stirring.

The pH is adjusted to 6.0-6.5 by addition of sodium hydroxide [INCI: SODIUM HYDROXIDE] (phase F), obtaining a cosmetic composition with the proportions shown in table 7.

TABLE 7

|   | INGREDIENT | % weight |
|---|---|---|
| A | WATER (AQUA) | 79.20 |
| A | PENTYLENE GLYCOL | 5.00 |
| A | BENZYL ALCOHOL | 0.40 |
| A | CARBOMER | 0.50 |
| A | POTASSIUM CETYL PHOSPHATE | 0.50 |
| B | ETHYLHEXYL COCOATE | 2.50 |
| B | GLYCERYL STEARATE | 2.05 |
| B | CETEARYL ALCOHOL | 2.05 |
| B | POTASSIUM PALMITOYL HYDROLYZED WHEAT PROTEIN | 0.90 |
| B | C12-15 ALKYL BENZOATE | 2.00 |
| B | DIMETHICONE | 1.00 |
| B | PHENOXYETHANOL | 0.80 |
| C | Lipid nanoparticles of example 7 | 2.00 |
| D | POLYACRYLAMIDE | 0.40 |
| D | WATER (AQUA) | 0.34 |
| D | C13-14 ISOPARAFFIN | 0.20 |
| D | LAURETH-7 | 0.06 |
| E | FRAGRANCE (PARFUM) | 0.10 |
| F | SODIUM HYDROXIDE 20% | q.s. |

Example 11: Study of the Decrease in the Relative Level of Nocturnin with an ELISA (Enzyme-Linked Immunosorbent Assay) Colorimetric Test, Using a Primary Human Subcutaneous Pre-Adipocyte Cell Line The decrease in the relative level of nocturnin in human pre-adipocytes in a complete differentiation medium (basal control) is studied when treating the exopolysaccharide of the strain of *Halomonas anticariensis* species with deposit number LMG P-27891 obtained in accordance with example 1.

Human pre-adipocytes are seeded (10,000 cells/well, 4 wells per condition) on a 96-well plate and incubated on a complete growth medium (PGM2, LONZA) for 24 hours at 37° C. at an atmosphere with a $CO_2$ level of 5%.

After incubation, the cells are treated with the exopolysaccharide at 10, 50, 100 and 1000 µg/ml and its respective vehicles prepared in a complete differentiation medium (PDM2, LONZA). After 6 days of treatment at an atmosphere with 37° C. and a 5% $CO_2$ level, the nocturnin level is measured using an ELISA test, and the total protein concentration is measured using a BCA (Bicinchoninic Acid) assay. For each concentration, the ELISA results are normalized with the BCA results. The relative nocturnin level is calculated from these results with respect to the basal control (cells treated with complete differentiation medium).

Measurement of Nocturnin Level (CCRN4L) with the ELISA (Enzyme-Linked Immunosorbent Assay) Test The manufacturer protocol of the ELISA kit for Carbon Catabolite Repression 4 Like Protein (CCRN4L) (Uscn Life Science Inc) is followed. In brief, the cells are lysed and the cell extracts are incubated on a 96-well plate coated with an anti-body specific to CCRN4L. Afterwards, the wells are coated with an antibody specific to CCRN4L conjugated with Biotin. Next, the Avidin conjugated with the enzyme Horseradish Peroxidase (HRP) is added to the plate. Finally 3,3',5,5'-Tetramethylbenzidine substrate is added to the plate and a change in color is observed proportionally to the quantity of nocturnin in each concentration. Lastly, a sulfuric acid solution is added to stop the enzyme-substrate reaction and quantify the color change with an absorbance reader (Multiskan-Thermo™ Electro Corporation) at 450 and 570 nm.

Determination of Total Protein by BCA Assay (Bicinchoninic Acid)

The manufacturer protocol of the BCA Protein assay kit (Pierce) is followed. The total protein concentration of the lysed cells is measured via a colorimetric reaction using a protein standard. In brief, the standard and the samples are distributed onto 96-well plates. The plate is then incubated with the reagent of the kit and finally the change in color is measured with the absorbance reader (Multiskan-Thermo™ Electro Corporation) at 570 nm.

The obtained results are shown below in table 8:

TABLE 8

| Product | Concentration | Nocturnin level with respect to basal control (%) |
| --- | --- | --- |
| Exopolysaccharide | 10 µg/mL | 82 ± 7% |
| Exopolysaccharide | 50 µg/mL | 67 ± 2% |
| Exopolysaccharide | 100 µg/mL | 58 ± 5% |
| Exopolysaccharide | 1000 µg/mL | 54 ± 2% |

The results show that the exopolysaccharide of the strain of *Halomonas anticariensis* species with deposit number LMG P-27891 reduces the relative level of nocturnin at all the concentrations studied, and it shows a Dose-Response relationship.

Example 12: Study on the Reduction of the Percentage of Lipid Accumulation (Adipogenesis) by a Fluorescent Assay for Determining Lipid Content Using a Primary Human Subcutaneous Pre-Adipocyte Cell Line The reduction of the percentage of lipid accumulation in human pre-adipocyte cells in a complete differentiation medium (basal control) is studied by treatment of the cells with the exopolysaccharide of the strain of *Halomonas anticariensis* species with deposit number LMG P-27891 obtained in accordance with example 1.

Human pre-adipocyte cells (LONZA) are seeded in quadruplicate (10,000 cells/well) on a 96-well plate and they are incubated on a complete growth medium for 24 hours at 37° C. at an atmosphere with 5% $CO_2$.

The differentiation of pre-adipocytes to adipocytes is induced by changing the complete growth medium (PGM2, LONZA) for the complete differentiation medium (PDM2, LONZA). The cells are treated with the exopolysaccharide at 10, 50, 100 or 1000 µg/mL, prepared in complete differentiation medium. After 8-days of treatment at 37° C. at an atmosphere with 5% $CO_2$, lipid accumulation is measured for each concentration by fluorescence with an AdipoRed™ assay (LONZA). The lipid accumulation percentage is calculated from these results with respect to the complete growth medium (differentiation negative control, 0%) and the complete differentiation medium (basal control, 100%).

Determination of Lipid Accumulation

Manufacturer protocol is followed for the use of AdipoRed™ Assay Reagent (LONZA). In brief, the cells are washed and the reagent AdipoRed is added diluted. After being incubated for 15 minutes in darkness and at room temperature, the Relative Fluorescence Units (RFUs) are measured using a fluorescence plate reader (Fluostar-BMG™), with excitation filter at 485 nm and emission filter at 530 nm.

The obtained results are shown in table 9:

TABLE 9

| Product | Concentration | % Lipid Accumulation |
| --- | --- | --- |
| Exopolysaccharide | 10 µg/mL | 77.70 ± 2.81% |
| Exopolysaccharide | 50 µg/mL | 61.07 ± 0.98% |
| Exopolysaccharide | 100 µg/mL | 62.60 ± 2.51% |
| Exopolysaccharide | 1000 µg/mL | 81.35 ± 4.08% |

The results show that the exopolysaccharide of the strain of *Halomonas anticariensis* species with deposit number LMG P-27891 reduces the percentage of lipid accumulation at 10, 50 and 100 µg/mL, demonstrating a Dose-Response relationship.

Example 13: Study on Lipolytic Activity by Increase in the Relative Level of Released Glycerol with a Fluorimetric Assay, Using a Primary Human Subcutaneous Pre-Adipocyte Cell Line Synchronized in Night Mode The increase in the relative level of glycerol released in human pre-adipocytes synchronized in night mode in buffer HBSS (Hank's Balanced Salt Solution) (basal control) treated with the exopolysaccharide of the strain of *Halomonas anticariensis* species with deposit number LMG P-27891, obtained in accordance with example 1 is studied.

The human pre-adipocytes are seeded (LONZA) (10,000 cells/well) on a 96-well plate and are incubated on a complete growth medium (PGM2, LONZA) for 24 hours at 37° C. at an atmosphere with 5% $CO_2$. Each concentrate is assayed in triplicate.

Then, the cells are treated with complete differentiation medium (PDM2, LONZA) for 6 days at 37° C. at an atmosphere with 5% $CO_2$.

After the differentiation period, the synchronization assay of adipocytes started to induce daily night/day cycles. In order to do so, the cells are submitted to alternate cycles of approximately 12 hours with melatonin (condition that mimics night) and 12 hours without melatonin (condition that mimics day) in PMD2 for 4 days (+/−; +/−; +/−; +/−).

Finally, the synchronized adipocytes are treated in night mode (presence of melatonin) for 6 hours with the exopolysaccharide at 100 and 1000 µg/ml, and its respective vehicles prepared in HBSS salt solution, at 37° C. at an atmosphere with 5% $CO_2$.

After the treatments in night mode, the level of free glycerol is determined from the cell supernatants for each concentration by fluorescence. The total protein concentration is measured by a BCA assay from the cell extracts. The results of free glycerol are normalized with the BCA results for each condition. The relative level of the released glycerol is then calculated with respect to the basal control (cells treated with HBSS salt solution) using these results.

Measurement of Released Glycerol Levels with a Fluorimetric Assay.

The manufacturer protocol for the detection of free glycerol assay kit (Abcam) is followed. In brief, the cell supernatants are incubated at 37° C. on a 96-well plate with the mixture of reagents of the kit, so that the free glycerol is enzymatically oxidized to generate a product that emitted fluorescence when reacted with the probe included in the kit.

The fluorescence is quantified with the FLUOstar Galaxy (BMG) reader (Excitation at 530 nm and Emission at 590 nm). The measurement of fluorescence is proportional to the quantity of free glycerol in each condition.

Measurement of the Total Protein Concentration Using BCA (Bicinchoninic Acid) Assay The manufacturer protocol of the BCA protein assay kit (Pierce) is followed. The total protein concentration in the lysed cell is determined using a colorimetric reaction, using a protein standard. In brief, the standard and the samples are seeded on a 96-well plate. Then, the plate is incubated with the reagent of the kit and lastly the color change is measured at 570 nm with the absorbance plate reader (Multiskan-Thermo™ Electro Corporation).

TABLE 10

| Product | Concentration | Relative level of released glycerol with respect to the basal control (%) |
|---|---|---|
| Exopolysaccharide | 100 µg/mL | 126.9 ± 5.5% |
| Exopolysaccharide | 1000 µg/mL | 139.6 ± 3.3% |

The results (Table 10) show that the exopolysaccharide of the strain of *Halomonas anticariensis* species with deposit number LMG P-27891, increases the relative level of glycerol released by the adipocytes synchronized in night mode at all the studied concentrations.

Example 14: In Vitro Assay for the Determination of Type I Collagen in Human Dermal Fibroblasts The stimulation of type I collagen synthesis, induced by cosmetic agents is assayed with an ELISA kit (Enzyme-Linked Immunosorbent Assay), using primary fibroblast cultures, as they are the skin's main collagen producers.

The human dermal fibroblasts are treated with trypsin and seeded at a density of $5 \times 10^4$ cells/well on 48-well plates. After 24 hours of incubation at 37° C., 5% $CO_2$ in a humidified atmosphere, new medium is added with the concentrations of the product to be tested in each well (exopolysaccharide is tested at 10, 5 and 1 µg/mL). Cells not treated with the products to be tested are used as controls. The cells are incubated for 48 additional hours at 37° C., 5% $CO_2$ in a humidified atmosphere. The medium is subsequently collected from each well to be analyzed with an ELISA test. A standard curve is created with type I collagen (Sigma) and the dilutions of said standard curve are transferred to 96-well plates along with the medium collected from the cells. The plates are left at 4° C. in a humidified atmosphere overnight. Then, the wells are washed three times with a wash solution of Phosphate buffered saline (PBS) with 0.05% Tween-20 (Sigma) and subsequently a PBS solution with 3% BSA (Sigma) is used to prevent the possible non-specific bindings of the primary anti-body. After the blocking, the wells are washed three times with the wash solution and the wells are incubated for 2 hours with an anti-type I collagen antibody (Sigma). After incubation, the wells are washed again and the secondary antibody IgG-HRP (Molecular Probes) is added for 1 hour. Once the incubation is finished, the wells are washed and the substrate OPD (Sigma) is added and it is left to react for 30 minutes under stirring. The reaction is quenched with the addition of a $H_2SO_4$ solution 3M and absorbance is read at a wave length of 490 nm in a TECAN GENios™ spectrophotometer plate reader.

Table 11 shows the percentage of type I collagen with respect to that observed in negative controls.

TABLE 11

| Product | Concentration | % Increase in type I collagen synthesis |
|---|---|---|
| Exopolysaccharide | 10 µg/mL | 37.2% |
| Exopolysaccharide | 5 µg/mL | 38.1% |
| Exopolysaccharide | 1 µg/mL | 45.4% |
| Control | 0.2 mg/mL | 0% |

The results show that the exopolysaccharide of the strain of *Halomonas anticariensis* species with deposit number LMG P-27891 increases the percentage of type I collagen synthesis at 1, 5 and 10 µg/mL.

Example 15: In Vitro Assay for Elastase Activity

Skin elasticity is a mechanical property influenced by elastin, a protein in the connective tissue of the dermis which. The metabolism of elastin decreases with the age and with the presence of elastase enzymes, enzymes responsible for breaking down elastin protein. The inhibition of elastase treats and/or prevents the loss of skin elasticity.

Elastase activity is measured with EnzChek™ Elastase Assay kit (Molecular Probes). The elastin provided by the kit is labelled with BODIPY® FL dye such that the conjugate's fluorescence is quenched. The non-fluorescent substrate can be digested by elastase to yield highly fluorescent fragments. That is, the higher fluorescence value, the higher elastase activity, and therefore, the lower the inhibition of elastase enzyme.

50 µl/well of the exopolysaccharide of the strain of *Halomonas anticariensis* species with deposit number LMG P-27891, obtained in accordance with example 1, at 10, 5, 2 and 1 mg/ml or reaction buffer alone (control) are added to a black 96-well microplate. Then, 50 µl of elastin solution labelled with BODIPY® FL dye are added to each well, as well as 100 µl of elastase enzyme solution diluted at 1 enzyme unit/ml. The plate is incubated at room temperature, protected from light, for 4-hour time, measuring fluorescence at multiple time points. The fluorescence is read at $\lambda_{exc}$=490 nm and $\lambda_{em}$=535 nm in a microtiter plate reader TECAN GENios™.

Table 12 shows the percentage of fluorescence respect to control.

TABLE 12

| Product | Concentration | % fluorescence respect to control |
|---|---|---|
| Control | | 100% |
| Exopolysaccharide | 10 mg/ml | 68.3% |
| Exopolysaccharide | 5 mg/ml | 79.3% |
| Exopolysaccharide | 2 mg/ml | 89.7% |
| Exopolysaccharide | 1 mg/ml | 93.9% |

The results show that the fluorescence decreases with the concentration of exopolysaccharide, and therefore, that the exopolysaccharide of the strain of *Halomonas anticariensis* species with deposit number LMG P-27891 inhibits the elastase activity.

Example 16: In Vitro Wound Healing Assay on Human Keratinocytes

Human keratinocytes are grown to confluence and then are treated with trypsin and seeded at a density of $5 \times 10^4$ cells/well at 48-well plates. After 48 hours of incubation at 37° C. in 5% CO$_2$ humidified air, a cell-free area is introduced by scraping the monolayer with a pipette tip. New medium is added with the exopolysaccharide of the strain of *Halomonas anticariensis* species with deposit number LMG P-27891, obtained in accordance with example 1, at 10 µg/ml concentration per well. Cells not treated with the exopolysaccharide are used as control. At this time, scrape wounds are photographed (time=0 hours) by using a Zeiss Axiovert 40 CFL microscopy and an AxioCam MRc5™ camera. Cells are allowed to migrate into the wound space for 48 h under standard culture conditions. After this time, new photographs of the cells are taken (time=48 hours). The percentage of wound healing respect to time zero is calculated by measuring free-cell area at each time.

Table 13 shows the percentage of wound healing respect to control.

TABLE 13

| Product | Concentration | % Increase of wound healing respect to control |
|---|---|---|
| Control | | 0% |
| Exopolysaccharide | 10 µg/ml | 40.1% |

The results show that the exopolysaccharide of the strain of *Halomonas anticariensis* species with deposit number LMG P-27891 increases the wound healing.

Example 17: Study of the Decrease in the Relative Level of Nocturnin with an ELISA (Enzyme-Linked Immunosorbent Assay) Colorimetric Test, Using a Primary Human Subcutaneous Preadipocyte Cell Line Synchronized in Night Mode Similarly to example 11, the decrease in the relative level of nocturnin in human preadipocytes synchronized in night mode is studied.

Human pre-adipocytes (LONZA) are seeded (10,000 cells/well, 4 wells per condition) on a 96-well plate and incubated on a complete growth medium (PGM2, LONZA) for 3 days at 37° C. at an atmosphere with a CO$_2$ level of 5%.

Synchronization of pre-adipocytes to induce daily night/day cycles is obtained by alternating incubations of approximately 12 hours in complete differentiation medium (PDM2, LONZA) with Melatonin 1 nM (condition that mimics night) and 12 hours in PDM2 without melatonin (condition that mimics day), at 37° C. in a CO$_2$ incubator (5% CO$_2$) during 4 days. Two incubation protocols with melatonin are followed in order to obtain synchronized cultures mimicking the night (+/−; +/−; +/−; +/−) and mimicking the day (−/+; −/+; −/+; −/+).

After four daily cycles, the synchronized cells are treated with the exopolysaccharide at 100 µg/ml or with the basal control for 6 hours in induced night (with melatonin) conditions, in a CO$_2$ incubator (37° C. and 5% CO$_2$). Then, the nocturnin level is measured using an ELISA test, and the total protein concentration is measured using a BCA (Bicinchoninic Acid) assay. For each concentration, the ELISA results are normalized with the BCA results. The relative nocturnin level is calculated from these results with respect to the basal control (cells treated with complete differentiation medium).

Measurement of Nocturnin Level (CCRN4L) with the ELISA (Enzyme-Linked Immunosorbent Assay) Test The manufacturer protocol of the ELISA kit for Carbon Catabolite Repression 4 Like Protein (CCRN4L) (USCN Life Science Inc.) is followed like in example 11.

Determination of Total Protein by BCA Assay (Bicinchoninic Acid)

The manufacturer protocol of the BCA Protein assay kit (Pierce) is followed like in example 11. The obtained result is shown in table 14:

TABLE 14

| Product | Concentration | Nocturnin level with respect to basal control (%) |
|---|---|---|
| Exopolysaccharide | 100 µg/mL | 78 ± 4% |

The result shows that the exopolysaccharide of the strain of *Halomonas anticariensis* species with deposit number LMG P-27891 reduces the relative nocturnin protein level in synchronized human adipocytes in induced night.

Example 18: Preparation of a Cosmetic Gel Cream Composition Comprising the Exopolysaccharide of the Strain of the *Halomonas anticariensis* Species with Deposit Number LMG P-27891

In an appropriate container, water [INCI: WATER (AQUA)], Hydrolite-5® 2/016020 [INCI: PENTYLENE GLYCOL], glycerine [INCI: GLYCERIN], Betafin® BP [INCI: BETAINE], Microcare® BNA [INCI: BENZYL ALCOHOL] and Carbopol® Ultrez 10 [INCI: CARBOMER] are mixed under stirring. Then, Arlatone® Map 160 K [INCI: POTASSIUM CETYL PHOSPHATE] is added until dispersion and the entire mixture is heated at 70-50° C. This mixture of ingredients constitutes phase A.

In another container, the phase B ingredients, Massocare® HD [INCI: ISOHEXADECANE], Finsolv® TN [INCI: C12-C15 ALKYL BENZOATE], cetyl alcohol [INCI: CETYL ALCOHOL], phenoxyethanol [PHENOXYETHANOL], Polysorbate 20 [INCI: POLYSORBATE 20], stearic acid [INCI: STEARIC ACID] and palmitic acid [INCI: PALMITIC ACID] are also dissolved at 70-75° C., and slowly added to phase A under turbine stirring.

Then, the mixture of phases A and B is cooled down to 50° C. and phase C is added.

Then, the only phase D component, the fragrance [INCI: FRAGRANCE (PARFUM)] is added, under rotor stirring, to the previous mixture until homogenization.

The pH is adjusted to 6.0-6.5 by addition of sodium hydroxide [INCI: SODIUM HYDROXIDE] (q.s. sufficient quantity to adjust to this pH) under stirring (phase E), obtaining a cosmetic composition with the proportions shown in table 3.

Phase F includes the exopolysaccharide of the strain of the *Halomonas anticariensis* species with deposit number LMG P-27891 of example 1, together with water [INCI: WATER (AQUA)], disodium hydrogenphosphate 12-hydrate [INCI: DISODIUM PHOSPHATE], sodium dihydrogenphosphate 2-hydrate [INCI: SODIUM PHOSPHATE], ZEMEA propanediol [INCI: PROPANEDIOL], Dermosoft® GMCY [INCI: GLYCERYL CAPRYLATE] and xanthan gum [INCI: XANTHAN GUM], and it is added to the mixture of the previous phases under stirring.

TABLE 15

| | INGREDIENT | % weight |
|---|---|---|
| A | WATER (AQUA) | 76.78 |
| A | PENTYLENE GLYCOL | 4.90 |
| A | GLYCERIN | 2.94 |
| A | BETAINE | 2.94 |
| A | BENZYL ALCOHOL | 0.39 |
| A | CARBOMER | 0.34 |
| A | POTASSIUM CETYL PHOSPHATE | 0.39 |
| B | ISOHEXADECANE | 1.96 |
| B | C12-C15 ALKYL BENZOATE | 1.96 |
| B | CETYL ALCOHOL | 1.76 |
| B | PHENOXYETHANOL | 0.88 |
| B | POLYSORBATE 20 | 0.78 |
| B | STEARIC ACID | 0.24 |
| B | PALMITIC ACID | 0.24 |
| F | WATER (AQUA) | 1.42 |
| F | PROPANEDIOL | 0.49 |
| F | DISODIUM PHOSPHATE | 0.03 |
| F | XANTHAN GUM | 0.02 |
| F | SODIUM PHOSPHATE | 0.02 |
| F | GLYCERYL CAPRYLATE | 0.01 |
| F | Exopolysaccharide from example 1 | 0.01 |
| C | CYCLOMETHICONE | 1.96 |
| D | FRAGRANCE (PARFUM) | 0.10 |
| E | SODIUM HYDROXIDE 20% | q.s. |

Example 18: Preparation of a Cosmetic Gel Cream Composition Comprising the Exopolysaccharide of the Strain of the *Halomonas anticariensis* Species with Deposit Number LMG P-27891

The composition is prepared according to the instructions of example 17, but with the following concentrations:

TABLE 16

| | INGREDIENT | % weight |
|---|---|---|
| A | WATER (AQUA) | 74.64 |
| A | PENTYLENE GLYCOL | 4.80 |
| A | GLYCERIN | 2.88 |
| A | BETAINE | 2.88 |
| A | BENZYL ALCOHOL | 0.38 |
| A | CARBOMER | 0.34 |
| A | POTASSIUM CETYL PHOSPHATE | 0.38 |
| B | ISOHEXADECANE | 1.92 |
| B | C12-C15 ALKYL BENZOATE | 1.92 |
| B | CETYL ALCOHOL | 1.73 |
| B | PHENOXYETHANOL | 0.86 |
| B | POLYSORBATE 20 | 0.77 |
| B | STEARIC ACID | 0.24 |
| B | PALMITIC ACID | 0.24 |
| F | WATER (AQUA) | 2.84 |
| F | PROPANEDIOL | 0.98 |
| F | DISODIUM PHOSPHATE | 0.06 |
| F | XANTHAN GUM | 0.04 |
| F | SODIUM PHOSPHATE | 0.04 |
| F | GLYCERYL CAPRYLATE | 0.02 |
| F | Exopolysaccharide from example 1 | 0.02 |
| C | CYCLOMETHICONE | 1.92 |
| D | FRAGRANCE (PARFUM) | 0.10 |
| E | SODIUM HYDROXIDE 20% | q.s. |

Example 19: Preparation of a Placebo Composition

The composition is prepared according to the instructions of example 17, but with water in the phase F and the following concentrations:

TABLE 17

| | INGREDIENT | % weight |
|---|---|---|
| A | WATER (AQUA) | 76.78 |
| A | PENTYLENE GLYCOL | 4.90 |
| A | GLYCERIN | 2.94 |
| A | BETAINE | 2.94 |
| A | BENZYL ALCOHOL | 0.39 |
| A | CARBOMER | 0.34 |
| A | POTASSIUM CETYL PHOSPHATE | 0.39 |
| B | ISOHEXADECANE | 1.96 |
| B | C12-C15 ALKYL BENZOATE | 1.96 |
| B | CETYL ALCOHOL | 1.76 |
| B | PHENOXYETHANOL | 0.88 |
| B | POLYSORBATE 20 | 0.78 |
| B | STEARIC ACID | 0.24 |
| B | PALMITIC ACID | 0.24 |
| F | WATER (AQUA) | 2 |
| C | CYCLOMETHICONE | 1.96 |
| D | FRAGRANCE (PARFUM) | 0.10 |
| E | SODIUM HYDROXIDE 20% | q.s. |

Example 20: Preparation of a Placebo Composition

The composition is prepared according to the instructions of example 17, but with water in the phase F and the following concentrations:

TABLE 18

| | INGREDIENT | % weight |
|---|---|---|
| A | WATER (AQUA) | 74.64 |
| A | PENTYLENE GLYCOL | 4.80 |
| A | GLYCERIN | 2.88 |
| A | BETAINE | 2.88 |
| A | BENZYL ALCOHOL | 0.38 |
| A | CARBOMER | 0.34 |
| A | POTASSIUM CETYL PHOSPHATE | 0.38 |
| B | ISOHEXADECANE | 1.92 |
| B | C12-C15 ALKYL BENZOATE | 1.92 |
| B | CETYL ALCOHOL | 1.73 |
| B | PHENOXYETHANOL | 0.86 |
| B | POLYSORBATE 20 | 0.77 |
| B | STEARIC ACID | 0.24 |
| B | PALMITIC ACID | 0.24 |
| F | WATER (AQUA) | 4 |
| C | CYCLOMETHICONE | 1.92 |
| D | FRAGRANCE (PARFUM) | 0.10 |
| E | SODIUM HYDROXIDE 20% | q.s. |

Example 21: In Vivo Study of Cosmetic Compositions Containing the Exopolysaccharide of the Strain of *Halomonas anticariensis* Species with Deposit Number LMG P-27891, for the Treatment of Cellulite in Female Volunteers The study is carried out for 30 days with measurements at initial time, after 15 days and after 30 days of treatment. A panel with 21 female subjects between 27 and 45 years old apply the composition of example 17 on the area of hips and thighs (left or right) and the placebo composition of example 19 on the other side. A second panel with 20 female subjects between 25 and 47 years old applies the composition of example 18 on the area of hips and thighs (left or right) and the placebo composition of example 20 on the other side. Cream is applied once a day, at night. The subjects serve as their own reference and results obtained at different times are compared with those obtained at initial time. The results obtained with the compositions of examples 17 and 19 are compared with the results obtained with placebo composition of examples 18 and 20, respectively.

The efficacy of the product is assessed by:

Reduction of thigh contours: obtained by image analysis of digital photos of thighs, results on table 19.

Smoothening of the skin relief: obtained by image analysis of digital photos, results on table 20.

Thermography of fat evenness: images of the buttocks and back of the thighs using a thermographic camera and analysis to obtain uniformity of the skin surface temperature, results on table 21.

Skin firmness: measured by cutometry of thighs, results on table 22.

Sensory analysis by clinical efficacy: performed by the researcher by giving a score for the intensity of cellulite. The improvement of skin aspect is calculated, results on table 23.

TABLE 19

| Composition | Thigh contour (cm), 15 days | Thigh contour (cm), 30 days |
|---|---|---|
| Example 18 | +0.1 | 0 |
| Example 17 | −0.6 | −1.1 |
| Example 20 | 0 | −0.1 |
| Example 19 | −0.9 | −1.5 |

TABLE 20

| Composition | Skin relief smoothening (%), 15 days | Skin relief smoothening (%), 30 days |
|---|---|---|
| Example 18 | −0.9 | −0.8 |
| Example 17 | +2.7 | +6.8 |
| Example 20 | 0 | +0.4 |
| Example 19 | +5.0 | +11.1 |

TABLE 21

| Composition | Uniformity of skin surface temperature (%), 15 days | Uniformity of skin surface temperature (%), 30 days |
|---|---|---|
| Example 18 | −3.5 | +6.5 |
| Example 17 | +13.6 | +29.5 |
| Example 20 | −5.9 | +5.8 |
| Example 19 | +24.2 | +39.4 |

TABLE 22

| Composition | Skin firmness (%), 15 days | Skin firmness (%), 30 days |
|---|---|---|
| Example 18 | −2.7 | −0.1 |
| Example 17 | +5.7 | +14.4 |
| Example 20 | −1.8 | +0.4 |
| Example 19 | +11.1 | +23.0 |

TABLE 23

| Composition | Improvement of skin aspect (%), 15 days | Improvement of skin aspect (%), 30 days |
|---|---|---|
| Example 18 | 0 | +6.2 |
| Example 17 | +5.6 | +12.5 |
| Example 20 | −1.0 | +5.0 |
| Example 19 | +7.1 | +18.4 |

The results show that the exopolysaccharide of the strain of *Halomonas anticariensis* species with deposit number LMG P-27891 reduces the thigh contour, smoothes the skin relief and improves the skin firmness and skin aspect at different concentrations.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

The invention claimed is:

1. A cosmetic composition for topical or transdermal application comprising a cosmetically effective quantity of the exopolysaccharide produced by a strain of *Halomonas anticariensis* species with deposit number LMG P-27891 and at least one cosmetically acceptable excipient and/or ingredient, wherein the exopolysaccharide has a composition by weight of 1% to 22% of glucose, 50% to 85% of mannose, 15% to 30% of rhamnose, up to 3% by weight galacturonic acid and up to 4%, by weight xylose, with the condition that the sum of the percentages does not exceed 100%, and wherein the composition:
   is in a formulation selected from the group consisting of creams, multiple emulsions, liquid crystals, anhydrous compositions, foams, gels, cream gels, hydroalcoholic solutions, hydroglycolic solutions, hydrogels, liniments, soaps, shampoos, conditioners, polysaccharide films, ointments, mousses, powders, bars, pencils, sprays, and aerosols; and/or
   is incorporated into a cosmetic delivery system and/or sustained release system or is adsorbed on a solid organic polymer or solid mineral support: and/or
   comprises liposomes, lipid nanoparticles, surfactant-phospholipid mixed micelles, or water-in-oil microemulsions containing the exopolysaccharide; and/or
   is incorporated into fabric, non-woven fabric or a medical device, wherein the medical device is selected from the group consisting of bandages, gauzes, dressings, adhesive patches, non-adhesive patches, occlusive patches, microelectric patches and face masks.

2. The cosmetic composition according to claim 1, wherein the at least one cosmetically acceptable excipient and/or ingredient is selected from the group consisting of agents that reduce the amount of nocturnin, agents inhibiting the nocturnin expression, lipolytic agents or agents stimulating lipolysis, venotonic agents, agents modulating PGC-1α expression, agents inhibiting the activity of PPARγ, agents which reduce the triglyceride content of adipocytes, anti-cellulite agents, agents delaying adipocyte differentiation, agents which diminish the sebum production, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents which inhibit neuronal exocytosis, anticholinergic agents, agents which inhibit muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor aggregation, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of components of the stratum corneum, ceramides, fatty acids, agents that inhibit collagen degradation, agents that inhibit matrix metalloproteinases, agents that inhibit elastin degradation, agents that inhibit serine proteases, agents stimulating fibroblast proliferation, agents stimulating keratinocyte proliferation, agents stimulating melanocyte proliferation, agents stimulating keratinocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, astringent agents, agents which inhibit the activity of PAR-2, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, agents acting on cell metabolism, agents to improve dermal-epidermal junction, agents inducing hair growth, hair growth inhibiting or retardant agents, hair loss retardant agents, preservatives, perfumes, cosmetic and/or absorbent and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof.

3. The cosmetic composition according to claim 1, wherein the exopolysaccharide excreted by the strain of *Halomonas anticariensis* species has a residence time between 4 and 10 minutes at a HPLC analysis with a chromatographic column for aqueous Size Exclusion Chromatography, with a particle size of 8 μm, a pore size of 50 Å and a length/Internal Diameter of 300 mm×7.5 mm, water with sodium acetate 0.1 M as eluent and flow rate 0.8 ml/min.

4. A method for cosmetic, non-therapeutic treatment and/or care of the skin comprising applying the cosmetic composition of claim 1 to the skin.

5. The method of claim 4, wherein the cosmetic, non-therapeutic treatment and/or care comprises at least one of: treatment of cellulite, treatment of reduction of lipid accumulation in the skin, stimulation of lipolysis in the skin, stimulation of collagen synthesis, treatment of skin aging, treatment of skin wrinkles, treatment for improving skin firmness, prevention of loss of skin firmness, and treatment for improving skin elasticity.

6. The method of claim 4, wherein the cosmetic, non-therapeutic treatment and/or care reduces the amount of nocturnin in skin cells.

7. A method for cosmetic, non-therapeutic treatment and/or care of the skin comprising applying a cosmetic composition of claim 1 to the skin, the cosmetic composition comprising liposomes, lipid nanoparticles, surfactant-phospholipid mixed micelles, or water-in-oil microemulsions containing the exopolysaccharide produced by the strain of *Halomonas anticariensis* species.

8. A method for treatment of skin wounds comprising applying the cosmetic composition of claim 1 to a skin wound.

9. The cosmetic composition of claim 1, wherein the at least one cosmetically acceptable excipient and/or ingredient comprises:
between 0.1 weight % and 20 weight % of an humectant selected from the group consisting of glycerin, propylene glycol, butylene glycol, pentylene glycol, caprylyl glycol, lactic acid, urea, and sodium hyaluronate;
between 0.1 weight % and 20 weight % of an emollient or skin conditioning agent selected from the group consisting of dimethicone, glyceryl stearate, caprylic/capric triglyceride, cetearyl alcohol, lecithin, C12-15 alkyl benzoate, squalane, lanolin, behenyl alcohol, tocopheryl acetate, panthenol, *Butyrospermum parkii* butter, retinyl palmitate, and retinol; and
between 0.1 weight % and 20 weight % of a surfactant selected from the group consisting of xanthan gum, sodium laureth sulfate, stearic acid, polysorbate 20, polysorbate 80, stearyl alcohol, cetyl alcohol, steareth-2, ceteareth-20, and cocamidopropyl betaine.

10. The cosmetic composition of claim 1, wherein the composition is in a cream formulation.

11. The cosmetic composition of claim 1, wherein the composition is in a gel or hydrogel formulation.

12. The cosmetic composition of claim 1, wherein the composition is in a cream gel formulation.

13. The cosmetic composition of claim 1, wherein the composition is in an anhydrous composition.

14. The cosmetic composition of claim 1, wherein the composition is in a hydroalcoholic solution.

15. The cosmetic composition of claim 1, wherein the composition is in a hydroglycolic solution.

16. The cosmetic composition of claim 1, wherein the composition is in a soap, shampoo, or conditioner.

17. The cosmetic composition of claim 1, wherein the composition is in a polysaccharide film.

18. The cosmetic composition of claim 1, wherein the composition is in an ointment, mousse, powder, bar, or pencil formulation.

19. The cosmetic composition of claim 1, wherein the composition is in a spray formulation.

20. The cosmetic composition of claim 1, wherein the composition is in an aerosol formulation.

21. The cosmetic composition of claim 1, wherein the composition is adsorbed on a solid organic polymer or solid mineral support.

22. The cosmetic composition of claim 1, wherein the composition comprises liposomes containing the exopolysaccharide.

23. The cosmetic composition of claim 1, wherein the composition comprises lipid nanoparticles containing the exopolysaccharide.

24. The cosmetic composition of claim 1, wherein the composition comprises surfactant-phospholipid mixed micelles containing the exopolysaccharide.

25. The cosmetic composition of claim 1, wherein the composition comprises a water-in-oil microemulsion containing the exopolysaccharide.

26. The cosmetic composition of claim 1, wherein the composition is incorporated into fabric, non-woven fabric or medical device, wherein the medical device is selected from the group consisting of bandages, gauzes, dressings, adhesive patches, non-adhesive patches, occlusive patches, microelectric patches and face masks.

* * * * *